US011058430B2

(12) United States Patent
Gorochow et al.

(10) Patent No.: US 11,058,430 B2
(45) Date of Patent: Jul. 13, 2021

(54) ANEURYSM DEVICE AND DELIVERY SYSTEM

(71) Applicant: DePuy Synthes Products, Inc., Raynham, MA (US)

(72) Inventors: Lacey Gorochow, Raynham, MA (US); Ariel Soto Del Valle, Raynham, MA (US); Juan Lorenzo, Raynham, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 183 days.

(21) Appl. No.: 15/989,725

(22) Filed: May 25, 2018

(65) Prior Publication Data

US 2019/0357914 A1 Nov. 28, 2019

(51) Int. Cl.
*A61B 17/12* (2006.01)
*A61M 25/00* (2006.01)
*A61B 90/00* (2016.01)
*A61B 17/00* (2006.01)

(52) U.S. Cl.
CPC .. *A61B 17/12113* (2013.01); *A61B 17/12031* (2013.01); *A61B 17/12145* (2013.01); *A61M 25/0021* (2013.01); *A61B 17/12172* (2013.01); *A61B 2017/00778* (2013.01); *A61B 2017/1205* (2013.01); *A61B 2090/3966* (2016.02); *A61M 2025/0004* (2013.01); *A61M 2025/0042* (2013.01); *A61M 2210/12* (2013.01)

(58) Field of Classification Search
CPC .......... A61B 17/12172; A61B 17/1214; A61B 17/12113; A61B 2017/12054; A61B 17/12145; A61B 17/12031; A61B 2090/3966; A61B 217/00778; A61B 2017/1205; A61M 25/0021; A61M 25/0054; A61M 2025/0042; A61M 2210/12; A61M 2025/0004
See application file for complete search history.

(56) References Cited

U.S. PATENT DOCUMENTS 2,849,002 A 8/1958 Oddo
3,480,017 A 11/1969 Shute
(Continued)

FOREIGN PATENT DOCUMENTS

CA 2395796 A1 7/2001
CA 2598048 A1 5/2008
(Continued)

OTHER PUBLICATIONS

Extended European Search Report dated May 2, 2019 in corresponding European Application No. 18214052.5.
(Continued)

*Primary Examiner* — Phong Song H Dang
(74) *Attorney, Agent, or Firm* — Troutman Pepper Hamilton Sanders LLP

(57) ABSTRACT

The present disclosure relates to a braid for treating an aneurysm. The braid can include a proximal expandable portion for positioning inside the aneurysm and sealing across a neck of the aneurysm. The braid can also include a distal expandable portion distal of the proximal expandable portion, the distal expandable portion for filling the aneurysm.

19 Claims, 10 Drawing Sheets

(56) References Cited

U.S. PATENT DOCUMENTS

| | | | |
|---|---|---|---|
| 4,085,757 A * | 4/1978 | Pevsner | A61B 17/12031 604/907 |
| 4,282,875 A * | 8/1981 | Serbinenko | A61B 17/12109 604/907 |
| 4,364,392 A * | 12/1982 | Strother | A61B 17/0057 606/195 |
| 4,395,806 A | 8/1983 | Wonder et al. | |
| 4,517,979 A * | 5/1985 | Pecenka | A61B 17/12109 604/907 |
| 4,545,367 A | 10/1985 | Tucci | |
| 4,836,204 A | 6/1989 | Landymore et al. | |
| 4,991,602 A | 2/1991 | Amplatz et al. | |
| 5,002,556 A | 3/1991 | Ishida et al. | |
| 5,025,060 A | 6/1991 | Yabuta et al. | |
| 5,065,772 A | 11/1991 | Cox, Jr. | |
| 5,067,489 A | 11/1991 | Lind | |
| 5,122,136 A | 6/1992 | Guglielmi et al. | |
| 5,192,301 A | 3/1993 | Kamiya et al. | |
| 5,261,916 A * | 11/1993 | Engelson | A61B 17/12022 606/108 |
| 5,304,195 A * | 4/1994 | Twyford, Jr. | A61B 17/12022 606/191 |
| 5,334,210 A | 8/1994 | Gianturco | |
| 5,350,397 A | 9/1994 | Palermo | |
| 5,423,829 A | 6/1995 | Pham et al. | |
| 5,624,449 A | 4/1997 | Pham et al. | |
| 5,645,558 A | 7/1997 | Horton | |
| 5,733,294 A | 3/1998 | Forber et al. | |
| 5,916,235 A | 6/1999 | Guglielmi | |
| 5,891,128 A | 7/1999 | Chin et al. | |
| 5,928,260 A | 7/1999 | Chin et al. | |
| 5,935,148 A | 8/1999 | Villar | |
| 5,941,249 A | 8/1999 | Maynard | |
| 5,951,599 A | 9/1999 | McCrory | |
| 5,964,797 A | 10/1999 | Ho | |
| 6,007,573 A | 12/1999 | Wallace et al. | |
| 6,024,756 A | 2/2000 | Pham | |
| 6,036,720 A | 3/2000 | Abrams | |
| 6,063,070 A | 5/2000 | Eder | |
| 6,063,100 A * | 5/2000 | Diaz | A61B 17/12022 606/191 |
| 6,063,104 A | 5/2000 | Villar | |
| 6,080,191 A | 6/2000 | Thaler | |
| 6,086,577 A | 7/2000 | Ken et al. | |
| 6,096,021 A | 8/2000 | Helm et al. | |
| 6,113,609 A | 9/2000 | Adams | |
| 6,123,714 A | 9/2000 | Gia et al. | |
| 6,168,615 B1 | 1/2001 | Ken | |
| 6,168,622 B1 | 1/2001 | Mazzocchi | |
| 6,193,708 B1 | 2/2001 | Ken et al. | |
| 6,221,086 B1 | 4/2001 | Forber | |
| 6,270,515 B1 | 8/2001 | Linden et al. | |
| 6,315,787 B1 | 11/2001 | Tsugita et al. | |
| 6,331,184 B1 * | 12/2001 | Abrams | A61B 17/12022 604/164.09 |
| 6,334,048 B1 | 12/2001 | Edvardsson et al. | |
| 6,346,117 B1 | 2/2002 | Greenhalgh | |
| 6,350,270 B1 | 2/2002 | Roue | |
| 6,375,606 B1 | 4/2002 | Garbaldi et al. | |
| 6,375,668 B1 * | 4/2002 | Gifford | A61B 17/12022 606/200 |
| 6,379,329 B1 * | 4/2002 | Naglreiter | A61B 17/12113 604/101.02 |
| 6,391,037 B1 | 5/2002 | Greenhalgh | |
| 6,419,686 B1 | 7/2002 | McLeod et al. | |
| 6,428,558 B1 * | 8/2002 | Jones | A61B 17/12022 606/151 |
| 6,454,780 B1 | 9/2002 | Wallace | |
| 6,463,317 B1 | 10/2002 | Kucharczyk et al. | |
| 6,506,204 B2 | 1/2003 | Mazzocchi et al. | |
| 6,527,919 B1 | 3/2003 | Roth | |
| 6,547,804 B2 | 4/2003 | Porter et al. | |
| 6,551,303 B1 | 4/2003 | Van Tassel et al. | |
| 6,569,179 B2 | 5/2003 | Teoh | |
| 6,569,190 B2 | 5/2003 | Whalen, II et al. | |
| 6,572,628 B2 | 6/2003 | Dominguez | |
| 6,589,230 B2 | 7/2003 | Gia et al. | |
| 6,589,256 B2 | 7/2003 | Forber | |
| 6,605,102 B1 | 8/2003 | Mazzocchi et al. | |
| 6,620,152 B2 | 9/2003 | Guglielmi | |
| 6,669,719 B2 | 12/2003 | Wallace et al. | |
| 6,689,159 B2 | 2/2004 | Lau et al. | |
| 6,746,468 B1 | 6/2004 | Sepetka | |
| 6,780,196 B2 | 8/2004 | Chin et al. | |
| 6,802,851 B2 | 10/2004 | Jones | |
| 6,811,560 B2 | 11/2004 | Jones | |
| 6,833,003 B2 | 12/2004 | Jones et al. | |
| 6,846,316 B2 | 1/2005 | Abrams | |
| 6,849,081 B2 * | 2/2005 | Sepetka | A61B 17/12022 606/1 |
| 6,855,154 B2 | 2/2005 | Abdel-Gawwad | |
| 6,949,116 B2 | 9/2005 | Solymar et al. | |
| 6,964,657 B2 * | 11/2005 | Cragg | A61B 17/12022 604/508 |
| 6,964,671 B2 | 11/2005 | Cheng | |
| 6,994,711 B2 * | 2/2006 | Hieshima | A61B 17/12022 606/108 |
| 7,044,134 B2 | 5/2006 | Khairkhahan et al. | |
| 7,083,632 B2 | 8/2006 | Avellanet | |
| 7,093,527 B2 | 8/2006 | Rapaport et al. | |
| 7,128,736 B1 | 10/2006 | Abrams et al. | |
| 7,152,605 B2 | 12/2006 | Khairkhahan et al. | |
| 7,153,323 B1 | 12/2006 | Teoh | |
| 7,195,636 B2 | 3/2007 | Avellanet et al. | |
| 7,229,454 B2 | 6/2007 | Tran et al. | |
| 7,229,461 B2 | 6/2007 | Chin et al. | |
| 7,309,345 B2 | 12/2007 | Wallace | |
| 7,371,249 B2 | 5/2008 | Douk et al. | |
| 7,410,482 B2 | 8/2008 | Murphy et al. | |
| 7,572,288 B2 | 8/2009 | Cox | |
| 7,597,704 B2 | 10/2009 | Frazier et al. | |
| 7,608,088 B2 | 10/2009 | Jones | |
| 7,695,488 B2 * | 4/2010 | Berenstein | A61B 17/12177 606/194 |
| 7,713,264 B2 | 5/2010 | Murphy | |
| 7,744,652 B2 | 6/2010 | Morsi | |
| 7,892,248 B2 | 2/2011 | Tran et al. | |
| 7,985,238 B2 * | 7/2011 | Balgobin | A61B 17/12113 606/200 |
| RE42,758 E | 9/2011 | Ken | |
| 8,016,852 B2 | 9/2011 | Ho | |
| 8,021,416 B2 | 9/2011 | Abrams | |
| 8,025,668 B2 | 9/2011 | McCartney | |
| 8,034,061 B2 | 10/2011 | Amplatz et al. | |
| 8,048,145 B2 | 11/2011 | Evans et al. | |
| 8,062,325 B2 * | 11/2011 | Mitelberg | A61F 2/95 606/200 |
| 8,075,585 B2 | 12/2011 | Lee et al. | |
| 8,142,456 B2 * | 3/2012 | Rosqueta | A61M 29/02 606/157 |
| 8,221,483 B2 | 7/2012 | Ford et al. | |
| 8,261,648 B1 | 9/2012 | Marchand et al. | |
| 8,267,923 B2 | 9/2012 | Murphy | |
| 8,361,106 B2 | 1/2013 | Solar et al. | |
| 8,361,138 B2 | 1/2013 | Adams | |
| 8,372,114 B2 | 2/2013 | Hines | |
| 8,398,671 B2 | 3/2013 | Chen | |
| 8,430,012 B1 | 4/2013 | Marchand | |
| 8,454,633 B2 | 6/2013 | Amplatz et al. | |
| 8,523,897 B2 | 9/2013 | van der Burg et al. | |
| 8,523,902 B2 * | 9/2013 | Heaven | A61B 17/0401 606/232 |
| 8,551,132 B2 * | 10/2013 | Eskridge | A61B 17/122 606/191 |
| 8,777,974 B2 | 7/2014 | Amplatz et al. | |
| 8,900,304 B1 * | 12/2014 | Alobaid | A61B 17/7097 623/17.12 |
| 8,974,512 B2 | 3/2015 | Aboytes et al. | |
| 8,992,568 B2 | 3/2015 | Duggal et al. | |
| 8,998,947 B2 | 4/2015 | Aboytes et al. | |
| 9,055,948 B2 | 6/2015 | Jaeger et al. | |
| 9,107,670 B2 | 8/2015 | Hannes | |

(56) References Cited

U.S. PATENT DOCUMENTS

| | | | |
|---|---|---|---|
| 9,161,758 B2 * | 10/2015 | Figulla | A61B 17/12031 |
| 9,232,992 B2 | 1/2016 | Heidner et al. | |
| 9,259,337 B2 * | 2/2016 | Cox | A61F 2/86 |
| 9,314,326 B2 | 4/2016 | Wallace et al. | |
| 9,351,715 B2 | 5/2016 | Mach | |
| 9,414,842 B2 | 8/2016 | Glimsdale et al. | |
| 9,526,813 B2 | 12/2016 | Cohn et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,096 B2 | 2/2017 | Kim et al. | |
| 9,561,125 B2 | 2/2017 | Bowman et al. | |
| 9,572,982 B2 | 2/2017 | Burnes et al. | |
| 9,579,104 B2 * | 2/2017 | Beckham | A61B 17/12113 |
| 9,579,484 B2 | 2/2017 | Barnell | |
| 9,585,642 B2 | 3/2017 | Dinsmoor et al. | |
| 9,585,669 B2 | 3/2017 | Becking et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,629,635 B2 | 4/2017 | Hewitt et al. | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,681,861 B2 | 6/2017 | Heisel et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 9,918,720 B2 | 3/2018 | Marchand et al. | |
| 9,955,976 B2 | 5/2018 | Hewitt et al. | |
| 10,130,372 B2 | 11/2018 | Griffin | |
| 10,307,148 B2 | 6/2019 | Heisel et al. | |
| 10,327,781 B2 | 6/2019 | Divino et al. | |
| 10,342,546 B2 | 7/2019 | Sepetka et al. | |
| 10,716,573 B2 * | 7/2020 | Connor | A61B 17/12163 |
| 2002/0068974 A1 * | 6/2002 | Kuslich | A61F 2/441 |
| | | | 623/17.11 |
| 2002/0082638 A1 | 6/2002 | Porter et al. | |
| 2002/0143349 A1 | 10/2002 | Gifford, III et al. | |
| 2002/0147497 A1 * | 10/2002 | Belef | A61F 2/4611 |
| | | | 623/17.12 |
| 2002/0188314 A1 | 12/2002 | Anderson et al. | |
| 2003/0028209 A1 * | 2/2003 | Teoh | A61B 17/12172 |
| | | | 606/191 |
| 2003/0120337 A1 | 6/2003 | Van Tassel et al. | |
| 2003/0171739 A1 | 9/2003 | Murphy et al. | |
| 2003/0176884 A1 | 9/2003 | Berrada et al. | |
| 2003/0181927 A1 | 9/2003 | Wallace | |
| 2003/0181945 A1 | 9/2003 | Opolski | |
| 2003/0195553 A1 * | 10/2003 | Wallace | A61B 17/12172 |
| | | | 606/200 |
| 2003/0216772 A1 | 11/2003 | Konya | |
| 2004/0034366 A1 | 2/2004 | van der Burg et al. | |
| 2004/0034386 A1 | 2/2004 | Fulton et al. | |
| 2004/0044391 A1 | 3/2004 | Porter | |
| 2004/0087998 A1 | 5/2004 | Lee et al. | |
| 2004/0098027 A1 | 5/2004 | Teoh et al. | |
| 2004/0127935 A1 | 7/2004 | Van Tassel et al. | |
| 2004/0133222 A1 | 7/2004 | Tran et al. | |
| 2004/0153120 A1 | 8/2004 | Seifert et al. | |
| 2004/0210297 A1 * | 10/2004 | Lin | A61B 17/7097 |
| | | | 623/1.11 |
| 2004/0254594 A1 | 12/2004 | Alfaro | |
| 2005/0021016 A1 | 1/2005 | Malecki et al. | |
| 2005/0021072 A1 | 1/2005 | Wallace | |
| 2005/0159771 A1 | 7/2005 | Petersen | |
| 2005/0177103 A1 | 8/2005 | Hunter et al. | |
| 2005/0251200 A1 | 11/2005 | Porter | |
| 2006/0052816 A1 | 3/2006 | Bates et al. | |
| 2006/0058735 A1 | 3/2006 | Lesh | |
| 2006/0064151 A1 | 3/2006 | Guterman et al. | |
| 2006/0106421 A1 | 5/2006 | Teoh | |
| 2006/0155323 A1 | 7/2006 | Porter et al. | |
| 2006/0155367 A1 | 7/2006 | Hines | |
| 2006/0167494 A1 | 7/2006 | Suddaby | |
| 2006/0247572 A1 | 11/2006 | McCartney | |
| 2007/0088387 A1 | 4/2007 | Eskridge et al. | |
| 2007/0106311 A1 | 5/2007 | Wallace et al. | |
| 2007/0208376 A1 | 6/2007 | Meng | |
| 2007/0162071 A1 | 7/2007 | Burkett et al. | |
| 2007/0167876 A1 * | 7/2007 | Euteneuer | A61M 25/09 |
| | | | 600/585 |
| 2007/0173928 A1 | 7/2007 | Morsi | |
| 2007/0186933 A1 | 8/2007 | Domingo | |
| 2007/0191884 A1 | 8/2007 | Eskridge et al. | |
| 2007/0233188 A1 | 10/2007 | Hunt et al. | |
| 2007/0265656 A1 | 11/2007 | Amplatz et al. | |
| 2007/0288083 A1 | 12/2007 | Hines | |
| 2008/0097495 A1 | 4/2008 | Feller, III et al. | |
| 2008/0103505 A1 * | 5/2008 | Fransen | A61B 17/7097 |
| | | | 606/92 |
| 2008/0281350 A1 * | 11/2008 | Sepetka | A61B 17/12172 |
| | | | 606/200 |
| 2009/0036877 A1 | 2/2009 | Nardone et al. | |
| 2009/0062841 A1 | 3/2009 | Amplatz et al. | |
| 2009/0099647 A1 | 4/2009 | Glimsdale | |
| 2009/0227983 A1 * | 9/2009 | Griffin | A61M 25/0068 |
| | | | 604/526 |
| 2009/0281557 A1 | 11/2009 | Sander et al. | |
| 2009/0287291 A1 * | 11/2009 | Becking | A61B 17/12113 |
| | | | 623/1.11 |
| 2009/0287297 A1 | 11/2009 | Cox | |
| 2009/0318941 A1 | 12/2009 | Sepetka | |
| 2010/0023046 A1 | 1/2010 | Heidner et al. | |
| 2010/0023048 A1 | 1/2010 | Mach | |
| 2010/0063573 A1 | 3/2010 | Hijlkema | |
| 2010/0063582 A1 | 3/2010 | Rudakov | |
| 2010/0069948 A1 * | 3/2010 | Veznedaroglu | A61B 17/12022 |
| | | | 606/194 |
| 2010/0168781 A1 | 7/2010 | Berenstein | |
| 2010/0324649 A1 | 12/2010 | Mattsson et al. | |
| 2011/0046658 A1 | 2/2011 | Connor et al. | |
| 2011/0054519 A1 | 3/2011 | Neuss | |
| 2011/0112588 A1 * | 5/2011 | Linderman | A61B 17/8855 |
| | | | 606/86 R |

(56) References Cited

U.S. PATENT DOCUMENTS

| | | |
|---|---|---|
| 2011/0137317 A1* | 6/2011 | O'Halloran ........ A61B 17/8855 606/92 |
| 2011/0152993 A1* | 6/2011 | Marchand ........ A61B 17/12172 623/1.2 |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1* | 6/2012 | Muller ............... A61B 17/8855 604/99.01 |
| 2012/0191123 A1* | 7/2012 | Brister ............ A61M 25/10186 606/191 |
| 2012/0283768 A1 | 11/2012 | Cox et al. |
| 2012/0310270 A1 | 12/2012 | Murphy |
| 2012/0323267 A1* | 12/2012 | Ren .................. A61B 17/12172 606/191 |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1* | 10/2013 | Lorenzo ............. A61B 17/1214 606/200 |
| 2013/0261730 A1 | 10/2013 | Bose et al. |
| 2013/0345738 A1 | 12/2013 | Eskridge |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0277013 A1 | 9/2014 | Sepetka et al. |
| 2015/0057703 A1 | 2/2015 | Ryan et al. |
| 2015/0209050 A1 | 7/2015 | Aboytes et al. |
| 2015/0272589 A1 | 10/2015 | Lorenzo |
| 2015/0313605 A1* | 11/2015 | Griffin .................. A61B 90/39 606/200 |
| 2015/0342613 A1 | 12/2015 | Aboytes et al. |
| 2015/0374483 A1 | 12/2015 | Janardhan et al. |
| 2016/0022445 A1* | 1/2016 | Ruvalcaba ....... A61B 17/12113 606/198 |
| 2016/0030050 A1 | 2/2016 | Franano |
| 2016/0192912 A1 | 7/2016 | Kassab et al. |
| 2016/0249934 A1* | 9/2016 | Hewitt ............ A61B 17/12177 606/200 |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero et al. |
| 2017/0079680 A1 | 3/2017 | Bowman |
| 2017/0079717 A1 | 3/2017 | Walsh et al. |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Laizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0114350 A1 | 8/2017 | Shimizu et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagil et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340333 A1 | 11/2017 | Badruddin et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140305 A1 | 5/2018 | Connor |
| 2018/0242979 A1* | 8/2018 | Lorenzo ........... A61B 17/12113 |
| 2018/0303531 A1 | 10/2018 | Sanders et al. |
| 2018/0338767 A1 | 11/2018 | Dasnurkar et al. |
| 2019/0008522 A1 | 1/2019 | Lorenzo |
| 2019/0110796 A1 | 4/2019 | Jayaraman |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223878 A1* | 7/2019 | Lorenzo ........... A61B 17/12031 |
| 2019/0223879 A1 | 7/2019 | Jayaraman |
| 2019/0328398 A1 | 10/2019 | Lorenzo |
| 2019/0365385 A1 | 12/2019 | Gorochow et al. |
| 2020/0268365 A1 | 8/2020 | Hebert et al. |

FOREIGN PATENT DOCUMENTS

| | | |
|---|---|---|
| CA | 2 431 594 A1 | 9/2009 |
| CN | 204 683 687 U | 10/2015 |
| DE | 102008015781 A1 | 10/2009 |
| DE | 102010053111 A1 | 6/2012 |
| DE | 102009058132 B4 | 7/2014 |
| DE | 10 2013 106031 A1 | 12/2014 |
| DE | 202008018523 U1 | 4/2015 |

(56) References Cited

FOREIGN PATENT DOCUMENTS

| | | |
|---|---|---|
| DE | 102011102955 B4 | 5/2018 |
| EP | 902704 B1 | 3/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2016-502925 A | 2/2015 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 2005020822 A1 | 3/2005 |
| WO | WO 2005074814 A2 | 8/2005 |
| WO | 2005117718 A1 | 12/2005 |
| WO | WO 2006034149 A2 | 3/2006 |
| WO | WO 2006052322 A2 | 5/2006 |
| WO | 2007/076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012/034135 A1 | 3/2012 |
| WO | WO 2012032030 A1 | 3/2012 |
| WO | WO 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2014029835 A1 | 2/2014 |
| WO | WO 2014110589 A1 | 7/2014 |
| WO | WO 2014137467 A1 | 9/2014 |
| WO | WO 2015073704 A1 | 5/2015 |
| WO | 2015/160721 A1 | 10/2015 |
| WO | 2015160721 A1 | 10/2015 |
| WO | 2015171268 A2 | 11/2015 |
| WO | WO 2015166013 A1 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | WO 2018051187 A1 | 3/2018 |

OTHER PUBLICATIONS

Extended European Search Report issued in corresponding European Patent Application No. 19 21 5277 dated May 12, 2020.

Altes et al., Creation of Saccular Aneurysms in the Rabbit: A Model Suitable for Testing Endovascular Devices. AJR 2000; 174: 349-354.

Schaffer, Advanced Materials & Processes, Oct. 2002, pp. 51-54.

* cited by examiner

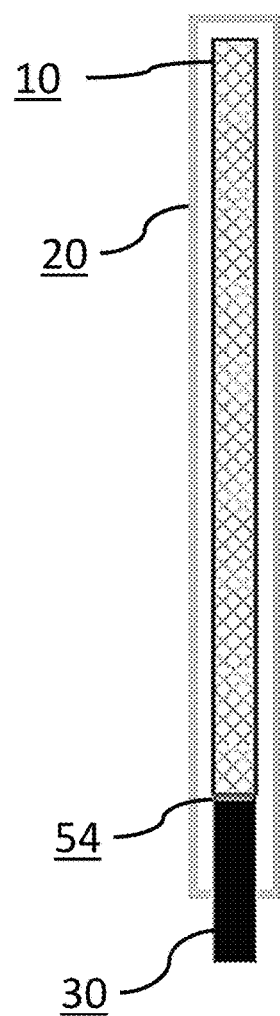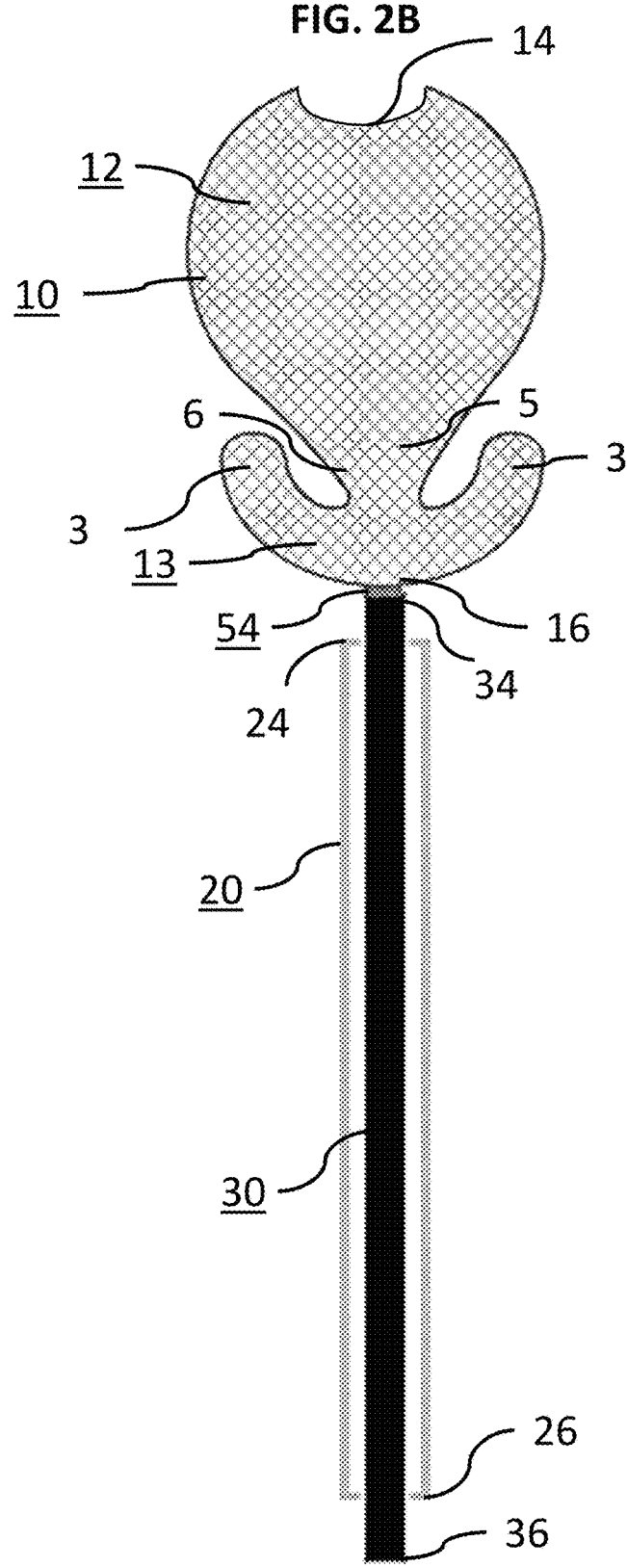

ANEURYSM DEVICE AND DELIVERY SYSTEM

FIELD

This disclosure relates to medical instruments, and more particularly, delivery systems for aneurysm therapy.

BACKGROUND

Aneurysms can be complicated and difficult to treat. For example, treatment access may be limited or unavailable when an aneurysm is located proximate critical tissues. Such factors are of particular concern with cranial aneurysms due to the brain tissue surrounding cranial vessels the corresponding limited treatment access.

Prior solutions have included endovascular treatment access whereby an internal volume of the aneurysm sac is removed or excluded from arterial blood pressure and flow. In this respect, because the interior walls of the aneurysm may continue being subjected to flow of blood and related pressure, aneurysm rupture remains possible.

Alternative to endovascular or other surgical approaches can include occlusive devices. Such devices have typically incorporated multiple embolic coils that are delivered to the vasculature using microcatheter delivery systems. For example, when treating cranial aneurysms, a delivery catheter with embolic coils is typically first inserted into non-cranial vasculature through a femoral artery in the hip or groin area. Thereafter, the catheter is guided to a location of interest within the cranium. The sac of the aneurysm can then be filled with the embolic material to create a thrombotic mass that protects the arterial walls from blood flow and related pressure. However, such occlusive devices do have certain shortcomings, including mass effect, which can cause compression on the brain and its nerves.

One particular type of occlusive approach endeavors to deliver and treat the entrance or "neck" of the aneurysm as opposed to the volume of the aneurysm by implanting a device in the parent vessel of the aneurysm. In such "neck" approaches, by minimizing blood flow across the neck, then a cessation of flow into the aneurysm may be achieved. In turn, a thrombotic mass may naturally form without having to deliver embolic materials into the aneurysm sac, as previously described. This approach is preferable to masses formed from embolic material since a natural mass can improve healing by reducing possible distention from arterial walls and permits reintegration into the original parent vessel shape along the neck plane of the aneurysm. It is understood that the neck plane is an imaginary surface where the inner most layer of the parent wall would be but for the aneurysm. However, neck-occlusive approaches, such as implanting a flow impeding device in the parent vessel, are not without drawbacks. Such an approach may impede blood flow into peripheral blood vessels while blocking the aneurysm neck in the parent vessel. Impeding flow to the peripheral blood vessel can unintentionally lead to severe damage if the openings of the vessels are blocked.

The solution of this disclosure resolves these and other issues of the art.

SUMMARY

In some embodiments, the present disclosure relates to a self-expanding braid for treating an aneurysm. The braid can include a proximal expandable portion for positioning inside the aneurysm and sealing across a neck of the aneurysm. The braid can also include a distal expandable portion distal of the proximal expandable portion, the distal expandable portion fills the aneurysm and provides an outward force on the proximal portion for it to remain in place in the aneurysm.

In some embodiments, the braid can move from a collapsed state within a microcatheter to a deployed state distal of the microcatheter.

In some embodiments, in the deployed state, the proximal expandable portion forms an annular expanded segment for sealing about the neck of the aneurysm and the distal expandable portion forms a distal sack for filling the aneurysm. The annular expanded segment can be formed from a single continuous portion or multiple separate, discrete portions (e.g. a plurality of expanded portions that extend from a proximal end of the braid).

In some embodiments, a porosity of the proximal expandable portion can be less than a porosity of the distal expandable portion. The respective porosities are defined by dimensions of interstices, braid angle, heat treatment, and/or covering.

In some embodiments, the distal sack can be shaped to be spherical, saddled, ellipsoid shaped, or any other shape. The distal sack can also be a collapsible cage-like vaso-occlusive structure.

In some embodiments, the annular expanded segment can form, invert about, and surround a lower end of the distal sack. In some embodiments, the annular expanded segment overlays the distal sack (e.g., overlays external to the distal sack). Outer ends or portions of the distal sack can be oriented to press against the inner surface of the annular expanded segment. Outer ends or portions of the distal sack can be oriented to press against the proximal segment as the braid expands into the deployed state. A gap or a cavity can form between the annular expanded segment and the distal sack when the distal sack is pressed against the annular segment, including against the inner surface of the annular expanded segment. A gap or a cavity can also be formed between the annular expanded segment and the distal sack when the annular expanded segment is inverted about the distal sack In some embodiments, the braid also includes a tapered segment disposed between the proximal and distal expandable portions. In this respect, the proximal expandable portion can include a porosity lower than a porosity of the tapered segment and/or the distal expandable portion. The proximal expandable portion can include an increased braid angle relative to a braid angle of the tapered segment and/or the distal expandable portion. The tapered segment can also include fewer wire segments than the proximal expandable portion and/or the distal expandable portion. In this respect, the proximal expandable portion, the distal expandable portion, and/or the tapered segment can have different braid properties.

In some embodiments, a buckle portion can be included in the braid that is defined between the tapered segment and the proximal expandable portion or the distal expandable portion.

In some embodiments, the braid has an open distal end and a proximal end of the braid is attached to a locking portion detachably connectable with a delivery tube.

In some embodiments, a system for treating an aneurysm is disclosed. The system includes a microcatheter, a delivery tube translatably disposed in the microcatheter, and a braid of this disclosure. The braid can be detachably connected to the delivery tube and slideably disposed within the microcatheter in a collapsed state and distally translatable from within the microcatheter to a deployed state. The braid can expand, including the distal and/or proximal expandable portions, to the deployed state as the distal end of the braid distally exits the microcatheter.

In some embodiments, the annular expanded segment overlays external to the distal sack as the braid distally translates from the microcatheter and the braid is pushed against the aneurysm wall.

In some embodiments, the system can include radiopaque entities such as platinum wires woven into the braid or drawn filled tube wires with platinum so that the device can be imaged under fluoroscopy. Including these entities will allow the end user to understand and visualize the location of the braid with respect to the aneurysm. An orientation and/or a position of the distal sack and/or the annular expanded segment can be adjustable by the braid being distally or proximally moved in the microcatheter.

In some embodiments, the system also includes a locking portion attached to a proximal end of the braid. In the collapsed state, the locking portion can be attached to a distal end of the delivery tube. In the deployed state, the locking portion can be detached from the delivery tube and the braid can be detached in the aneurysm.

In some embodiments, a method of delivering an occlusive device to an aneurysm, is also disclosed. The method can include attaching a proximal end of the braid to a distal end of a delivery tube; positioning a braid within a microcatheter; selectively positioning the braid with attached delivery tube in the vasculature (e.g. at the neck of the aneurysm); distally sliding the braid from a microcatheter, by the delivery tube, towards the aneurysm thereby expanding a distal expandable portion inside the aneurysm to form a distal sack and forming an annular expanded segment at a proximal end of the braid about the distal sack; releasing the braid, and withdrawing the delivery tube and the microcatheter from the aneurysm.

In some embodiments, filling the aneurysm by forming the distal sack.

In some embodiments, the selectively positioning of the braid comprises placing a distal end of the microcatheter at the neck of the aneurysm.

In some embodiments, the distal expandable portion is simultaneously expanding when the annular expanded segment is forming.

In some embodiments, the proximal segment expands after the distal segment is expanded.

In some embodiments, the method also includes attaching the locking portion at the proximal end of the braid and the distal end of the delivery tube; and releasing, by the locking portion, the delivery tube from the braid.

In some embodiments, the method also includes expanding the annular expanded segment so that the annular expanded segment overlays an outer surface of the distal sack.

In some embodiments, the method also includes pressing one or more outer ends of the distal sack against the annular expanded segment (e.g., the inner surface of the annular expanded segment) as the braid distally translates into the aneurysm.

In some embodiments, the method also includes forming a gap or a cavity between the annular expanded segment and the distal sack when the distal sack presses against the inner surface of the annular expanded segment.

In some embodiments, the method also includes forming a gap or a cavity between the annular expanded segment and the distal sack when the annular expanded segment inverts about the outer surface of the occlusive sack.

In some embodiments, the method also includes forming a tapered segment between the proximal and distal expandable portions. The method can also include making a porosity of the proximal expandable portion less than a porosity of the tapered segment and/or the distal expandable portion; positioning the proximal expandable portion adjacent or in communication with a neck of the aneurysm; and deflecting, diverting, and/or slowing a flow into the aneurysm. The method can also include making a flexibility of the proximal expandable portion less than a flexibility of the tapered segment and/or the distal expandable portion; positioning the proximal expandable portion adjacent or in communication with a neck of the aneurysm; and deflecting, diverting, and/or slowing a flow into the aneurysm. In some embodiments, the distal sack provides added flow diversion effect by providing another braid layer that blood has to flow through. The annular segment and proximal end of the distal sack may also provide an increased flow diversion effect as the blood has to flow through additional layers (e.g., three layers) of net like structures that comprise tiny pores.

In some embodiments, a method of using a braid for treating an aneurysm is disclosed. The method can include positioning the braid inside the aneurysm; distally moving the braid into the aneurysm; expanding a proximal expandable portion of the braid from a collapsed state to an expanded state thereby sealing a neck of the aneurysm; and expanding a distal expandable portion of the braid inside the aneurysm to form a distal sack thereby filling the aneurysm.

In some embodiments, the step of expanding the proximal expandable portion of the braid can include forming an annular expanded segment at a proximal end of the braid about the distal sack.

In some embodiments, the method can include overlaying the annular about an outer surface of the distal sack; and pressing outer ends of the distal sack against the inner surface of the annular segment as the braid expands into the deployed state to secure the device against the aneurysm wall.

In some embodiments, the method can include forming a gap or a cavity between the annular expanded segment and the distal sack when the distal sack presses against the annular segment.

In some embodiments, the method can include forming a tapered segment between the proximal and distal expandable portions. The method can also include making a porosity of the proximal expandable portion less than a porosity of the tapered segment and/or the distal expandable portion; and deflecting, diverting, and/or slowing a flow into the aneurysm. The method can also include making a flexibility of the proximal expandable portion less than a flexibility of the tapered segment and/or the distal expandable portion; and deflecting, diverting, and/or slowing a flow into the aneurysm.

Other aspects and features of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 2A is a schematic side view of an exemplary delivery system with an occlusive device collapsed within a microcatheter.

FIG. 2B is a schematic side view of an exemplary delivery system with an occlusive device deployed distal of a microcatheter.

DETAILED DESCRIPTION

Figure 1:
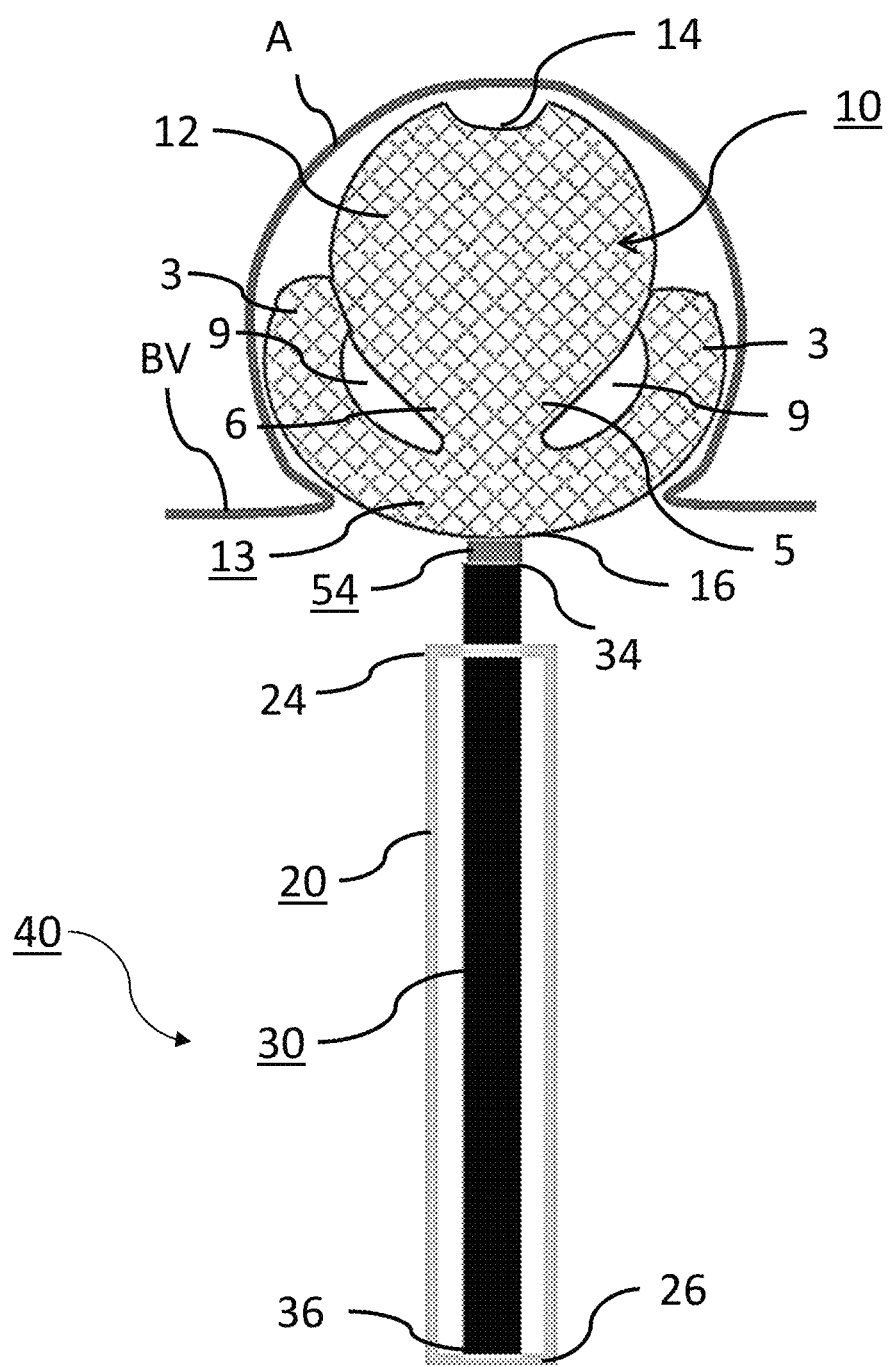
FIG. 1 depicts an example occlusive device of this disclosure deployed into an aneurysm.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature can be that of any "subject" or "patient" including of any human or animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a braid body to the vasculature of a subject.

Relatedly, flow diverters that are deployed across the aneurysm neck can alter the flow of blood into the aneurysm. An example flow diverter can be a braided device with relatively low porosity. Over time, the aneurysms can heal by sealing the aneurysm neck with a high rate of success. However, flow diversion technology is not without limitations. Challenges include placement of the devices intravascularly due to vessel morphology, vessel tortuosity, or braid malapposition. In addition, patients receiving a flow diverter must be on anticoagulation medicine for an extended period to prevent vessel thrombosis. Intrasaccular devices also aim to cut circulation into the aneurysm while minimizing the amount of metal in the vessel and significantly cutting or eliminating the need for coagulation medication. These types of devices may also be easier to track and/or deploy at the lesion site.

Devices and systems disclosed herein addresses these and other drawbacks of previous approaches by using a single device to seal the aneurysm neck, in the aneurysm and not in the parent vessel. Turning to FIG. 1, an example braid 10 of this disclosure is shown deployed into an aneurysm A of blood vessel BV but not yet released from delivery system 40. The delivery system 40 can include a microcatheter 20 with a delivery tube 30 slideably disposed therein. Braid 10 can be moved by delivery tube 30 from a collapsed state within microcatheter 20 to a deployed state distal of the microcatheter 20 as in FIG. 1. A distal end 34 of delivery tube 30 may be attached to a proximal end 16 of braid 10 through a locking portion 54, as described more particularly below.

In FIG. 1, the microcatheter 20 has been delivered to the neck of aneurysm A and a distal sack formed by distal expandable portion 12 of braid 10 is shown filling aneurysm A. Portion 12 can be radially expanded form the distal sack in a predetermined shape and structure that outlines and supports the walls of the aneurysm A. For example, the distal sack of portion 12 can be shaped to be spherical, saddled, ellipsoid shaped, or any other shape. The distal sack of portion 12 can also be a collapsible cage-like vaso-occlusive structure. An annular expanded segment 3 is also shown formed by proximal expandable portion 13, portion 13 being proximal of portion 12. Segment 3 can be formed about the neck of aneurysm A. In some embodiments, segment 3 can be for positioning inside and sealing across the neck of the aneurysm A. Segment 3 can be formed from a single continuous portion (e.g. a single integrally formed mesh) or multiple separate, discrete portions (e.g. a plurality of discrete portions capable of expanding and extending from a proximal end 16 of the braid 10).

When moving to the deployed state, portion 13 can expand and form annular expanded segment 3 about and/or surrounding a lower proximal end of the distal sack of portion 12. For example, annular expanded segment 3 can form about and/or surround a tapered segment 5 that may be positioned between portions 12 and 13. Though only portions 12 and 13 are depicted interconnected with tapered segment 5, any number of additional expandable portions and/or segments could be included as needed or required. Braid 10 can be formed from multiple self-expanding multifilament segments that can be formed from a mesh. Braid 10 can also include a buckle portion for facilitating expansion of portions 12 and/or 13 from collapsed to deployed states inside the aneurysm. One or more buckle portions 6 can be positioned between portions 12 and 13, including on or about the tapered segment 5. Braid 10 can also have an open distal end 14 associated with segment 12 and a proximal end 16 associated with segment 13 intended to be positioned on or adjacent the neck of the aneurysm A. End 16 can also be attached to locking portion 54 that is configured for releasable attachment with distal end 34 of delivery tube 30.

The mesh of braid 10 can be defined by one or more mesh patterns, one or more discrete mesh portions, including portions 12 and 13 and/or tapered segment 5, and/or one or more mesh openings defined by braided filaments. For example, the mesh of braid 10 can include a porosity region associated with the distal sack of portion 12 and another porosity region associated with segment 3 of portion 13. In some embodiments, a porosity of portion 12 can be less than a porosity of portion 13. However, braid 10 is not so limited and other parts of braid 10 can have their porosities and other braid properties varied as needed or required. For example, portion 13 can include a porosity lower than a porosity of tapered segment 5. The respective porosities of the various portions of braid 10 can be defined by varying dimensions of interstices, braid angle, heat treatment, mesh openings, covering, and/or the like. For example, the mesh of braid 10 shown in FIGS. 1 to 2B can include a different porosity region associated with each of segments 12, 13. In practice, the porosity of portion 12 can permit its outer distal sack to take on many shapes prior to, during, or after delivery to aneurysm In some embodiments, segment 3 can overlay the distal sack of portion 12 in the deployed state. For example, segment 3 can overlay the outer surface of the distal sack of portion 12 as the braid 10 is distally translated by delivery tube 30 from microcatheter 20. Expansion of portions 12 and 13 can also occur as braid 10 is pushed against the aneurysm wall. Outer ends of distal sack of portion 12 can also be oriented to press against the annular expanded segment 3 as the braid 10 expands into the deployed state. Exemplary "pressing" is shown in the depicted orientation of FIG. 1 whereby a gap or a cavity 9 can form between segment 3 and the distal sack when segment 12 is pressed against the inner surface of the annular segment of portion 3. This gap or cavity 9 can serve as an "air cushion" so that as braid is distally pushed deeper into the aneurysm A, rupture is avoided since portions 12 and 13 have certain amount of give by being be pushed into the other and flexibly conform to the shape of aneurysm A.

The mesh of braid 10 can be comprised of a tube with proximal end 16 opened at opposite distal end 14. Proximal end 16 may also be closed and attached to locking portion 54. Braid 10 can be made of several materials such as deposited thin films or of one single material. The mesh of braid 10 can include multiple wires, for example from 4 to 96 wires. The number of wires can be a factor in controlling material properties of the braid 10, including the porosity, shape in the deployed state, flexibility, stiffness, and the like. The combination of the distal sack of portion 12 with the annular expanded segment 3 externally overlaid therewith can be considered when determining the number of wires of the mesh of braid 10 since the sack is essentially inside annular expanded segment 3 in the deployed state. Further, the distal sack of segment 12 and/or the annular expanded segment 3 of portion 13 can together be a collapsible cage-like vaso-occlusive structure.

The wires of braid 10 can be made from nitinol with interwoven platinum filaments for radiopacity or Drawn Filled Tube (DFT) Nitinol with 10 to 40% Platinum. The wires can be made from a nickel-titanium alloy, cobalt chromium alloys, Stainless Steel, Tantalum, and/or other alloys, and/or any other suitable biocompatible materials, or combination of these materials. Also, these materials can be absorbable or non-absorbable by the patient over time. In this respect, the first porosity associated with portion 12 can be less than the porosity of portion 13. Arranging segments 12, 13 in the deployed state, varying the braid properties, and/or positioning segment 12 adjacent or in communication with a neck of the aneurysm can deflect, divert, and/or slow a flow into the aneurysm.

The apertures throughout the mesh of braid 10 can also create a substantially unitary frame work or mesh. Thus, the apertures may be of any size, shape, or porosity, and may be uniformly or randomly spaced throughout the wall of the mesh of braid 10. The apertures can provide braid 10 with flexibility and also assist in the transformation of the mesh from the collapsed state to the expanded, deployed state, and vice versa.

In certain embodiments, the braid angle of one or some of portions 12, 13 or tapered segment 5 can also vary. The wire diameter, pick count (i.e. the number of wire crossovers per lineal measurement) of braid 10 can also vary or otherwise be modified between locations of braid 10 to change the device characteristics as well as the heat set shape. The fibers of braid 10 can be formed by being fastened at their free ends by heat bonding by laser or ultrasonic weld, solvent or adhesive binding, crimping, or any other attachment means. The fibers of braid 10 may be bonded at their internal crossover points by solvent, adhesive, or heat bonding like laser, ultrasonic weld, or any other source of heat. However, braid 10 is not so limited and it can have a braid angle, pitch count, wire diameter, porosity or any other property of braid 10 that is substantially similar throughout.

Turning to FIG. 2A, an example braid 10 is shown in the collapsed state within microcatheter 20 and connected to delivery tube 30 prior to being arranged with aneurysm A. FIG. 2B depicts braid 10 of FIG. 2A connected to delivery tube 30 and arranged in the deployed state distal of the microcatheter 20. The delivery system 40 can include the microcatheter 20 with a delivery tube 30 slideably disposed therein. The microcatheter 20 can be pre-placed at the level of the aneurysm neck and used to track the device to the aneurysm. The microcatheter 20 size can be selected in consideration of the size, shape, and directionality of the aneurysm or features through which the microcatheter 20 must pass to get to the treatment site. The microcatheter 20 may have a total usable length anywhere from 80 centimeters to 170 centimeters. The microcatheter 20 may have an inner diameter ID of anywhere between 0.015 and 0.032 inches. The outer diameter OD may also range in size and may narrow at either its proximal end or distal end. At its proximal end 26, the microcatheter 20 may be operated by hand, and at its distal end 24 may be operable to positioned at the neck of the aneurysm A. While the distal end 24 of the microcatheter 20 as shown contains the braid 10, the end 24 may be varied in shape and may curve at an angle.

Delivery tube 30 can be substantially elongate and can extend from the proximal 26 to the distal end 24 of microcatheter 20. Tube 30 can generally run along the inner lumen of microcatheter 20 and may leave a space between its outer surface and the internal surface of microcatheter 20. In turn, delivery tube 30 and microcatheter 20 may be axially aligned. System 40 can deliver braid 10 to a location of interest (e.g. a lesion site) using microcatheter 20. In certain embodiments, microcatheter 20 can be pre-placed at a level of the aneurysm neck and used to track the braid 10 to the lesion, for example by tracking radiopaque elements associated with locking portion 54. Delivery tube 30 can be in mechanical connection with braid 10 at locking portion 54. As shown more particularly below, locking portion 54 can comprise a pusher ring.

Braid 10 may be attached to locking portion 54 by slidable attachment, permanent attachment (e.g. crimped, laser, ultrasonic weld, or other sources of heat, adhesive, or the like) or other attachment approaches, as described more particularly below. When delivery tube 30 is attached to braid 10 at locking portion 54, distally translating, sliding, or otherwise moving tube 30 towards the aneurysm A can cause braid 10 to begin moving from the collapsed state within microcatheter 20 to its deployed state external to microcatheter 20 with the formed distal sack of portion 12, the annular expanded segment 3 of portion 13, and/or tapered segment 5 disposed therebetween.

As shown in FIG. 2B, the respective sack of portion 12 is formed now deployed and annular expanded segment 3 of portion 13 is disposed proximal and externally overlaid of portion 12. Proximal end 16 is still connected to delivery tube 30 via locking portion 54. In FIG. 2B, the distal end 14 can form the outer layer of the distal sack of portion 12 while the proximal end 16 can form the outer layer of the annular expanded segment 3 of portion 13.

Figure 3:
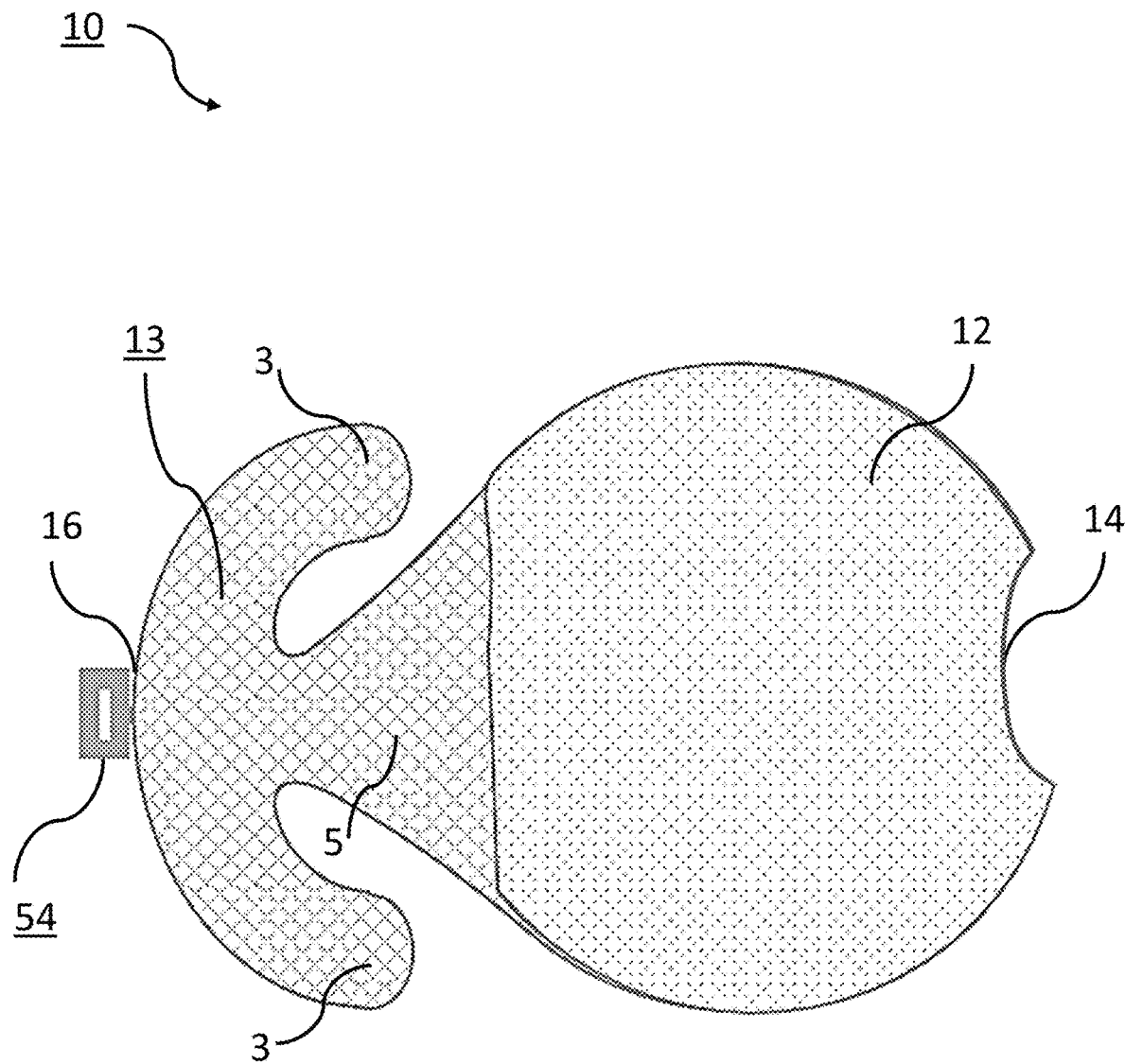
FIG. 3 is an enlarged schematic side view of the braid of FIGS. 1-2 in an expanded state.

Turning to FIG. 3, an enlarged schematic side view of the braid 10 of FIGS. 1-2B is shown in a close-up, expanded state. As shown, portion 12 has been expanded to a generally spherical shaped distal sack along with a proximal tapered cone segment 5 leading to the annular expanded segment 3 of portion 13. The mesh properties of braid, including porosity and flexibility, associated with portions 12, 13 and/or tapered segment 5 can vary, with the porosity being lowest and flexibility greatest preferably at portion 13 about the neck of the aneurysm. For example, portions of braid 10 on or proximate end 16 (e.g. portion 13) may be more pliable than portions of braid 10 on or proximate end 14 (e.g. portion 12) in order to induce self-expansion during delivery as the deployed shapes of portions 12 and 13 forms their respective predetermined shapes within aneurysm A (see, e.g., the distal sack of portion 12). However, braid 10 is not so limited and any combination of flexibility and/or porosity can be used as needed or required with portions 12, 13 and/or segment 5. Filaments in other porosity regions of braid 10 can also have a constant pick count throughout its length.

Braid 10 can be made from nitinol with interwoven platinum filaments for radiopacity. The tapered segment 5 between portions 12 and 13 can allow respective portions to expand to form the distal of portion 12 and surrounding annular expanded segment 3 of portion 13, as the device 10 is fully deployed in the aneurysm A. To facilitate expansion of the braid 10 and/or formation of the annular expanded segment of portion 13, the braid 10 can be modified to be weakened at segment 5 to facilitate inversion of segment 13 about segment 12. For example, segment 5 can include a pre-weakened portion that includes a localized braid angle change, removal of wire segments, localized heat treatment, and/or other approaches to change braid properties. In certain embodiments, the braid angle of portion 13 can be reduced relative to other portions, including portion 12, of braid 10 so that the flow can deflected, diverted, and/or slowed into the aneurysm. This is because portion 13 can be configured for communication with the neck of the aneurysm A when portions 12 and/or 13 expand and braid 10 is deployed in the aneurysm A, since end 16 can be tucked into segment 13 during delivery (e.g., see FIG. 6A).

The diameter of the braid 10 and the braid wire count can vary depending the diameter of the device needed to treat a specific aneurysm and/or the desired porosity. For example, to induce formation of the predetermined shape and strength of the distal sack of portion 12 and the annular expanded segment 3 of portion 13, end 14 may be more flexible than end 16, or vice versa, and other locations of braid 10 (e.g. tapered segment 5) may vary from most pliable on or about end 16 and less pliable on or about end 14. In some embodiments, braid wire ends of 14 can be looped about each other, which is particularly advantageous to ensure that the braid 10 is atraumatic when in contact with the dome of aneurysm A.

To form or assemble braid 10 as shown in FIGS. 1-3, locking portion 54 can be connected to and/or folded over end 16. Braid 10 is not so limited and end 16 can be operatively connected locking portion 54 or any other feature by sonic weld, mechanical attachment, or adhesive. Regardless of connection, the proximal end 16 being operatively connected to locking portion 54, can cause formation of an outer layer of the braid 10 associated with segment 12.

Figure 4:
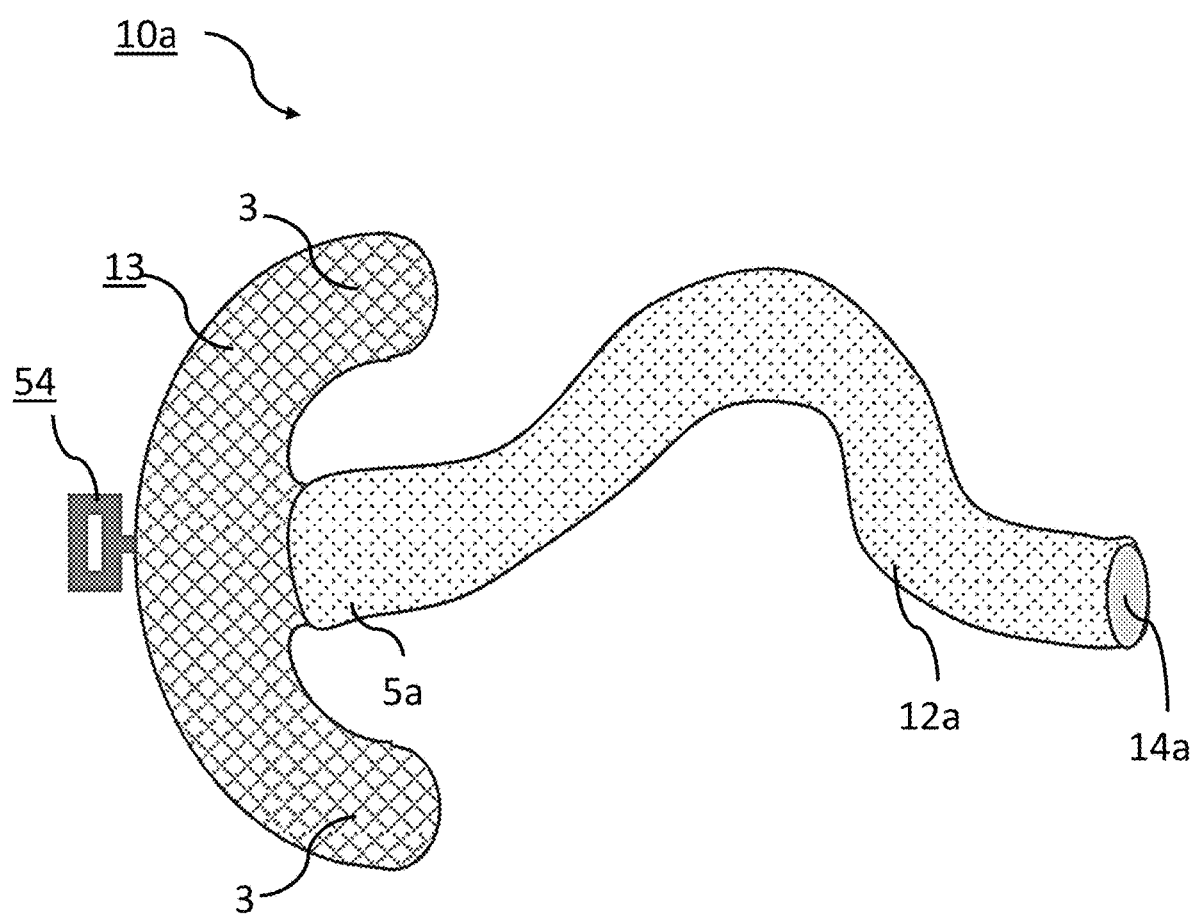
FIG. 4 is an enlarged schematic side view of another embodiment of a braid of this disclosure.

FIG. 4 is an enlarged schematic side view of an alternative braid 10a prior to being assembled with microcatheter 20 and delivery tube 30. In this embodiment, braid 10a can include an alternative portion 12a with open or closed distal end 14a opposite centrally disposed segment 5a and portion 13. Portion 12a as illustrated can be a simple tubular and/or cylindrical section designed to expand and take space inside the aneurysm A in a manner similar to a coil. The differences between the mesh characteristics of portions 12a and 13 are visible. It can also be seen that segment 3 of portion 13 in this embodiment can include atraumatic outer ends that are configured to expand and press against the aneurysm wall during delivery without risk of rupturing the aneurysm. Locking portion 54 can also be disposed at the proximal end 16 of braid 10a and include radiopaque elements to facilitate precise tracking to the lesion site. The depicted tortuous shape of portions 12a and 13 in the illustrated embodiment is merely exemplary and any shape for any feature of braid 10a, including portions 12a and 13, can be used as needed or required.

In practice, as shown in FIGS. 5A to 6B, the braid 10 can be pushed into the aneurysm A by the delivery tube 30 and be deployed with the lower porosity outer layer of portion 13 laying across the neck of the aneurysm A. Prior to the arrangement of FIG. 5A, the braid 10 can be assembled with a delivery tube 30 and/or a microcatheter 20 in a collapsed state and thus disposed inside microcatheter 20. In this respect, the delivery system 40 and braid 10 can be packaged as a portable kit or system. The assembly between microcatheter 20, delivery tube 30, and/or braid 10 can take place before being introduced into the vasculature. The delivery system 40 used with braid 10, which can include microcatheter 20 and delivery tube 30, can be selectively positioned at the lesion site and delivery tube 30 can begin distally translating braid 10 towards the aneurysm.

Figure 5A:
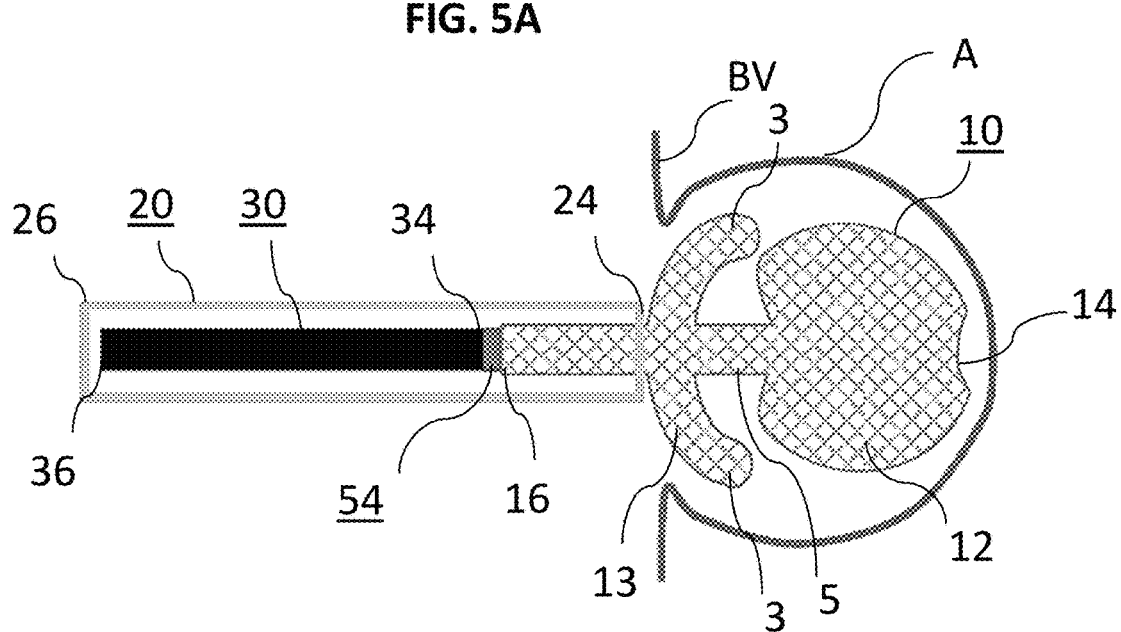
FIG. 5A is an enlarged schematic side view of the delivery system and braid of FIGS. 1-3 as the braid is being pushed into an example aneurysm.
Figure 5B:
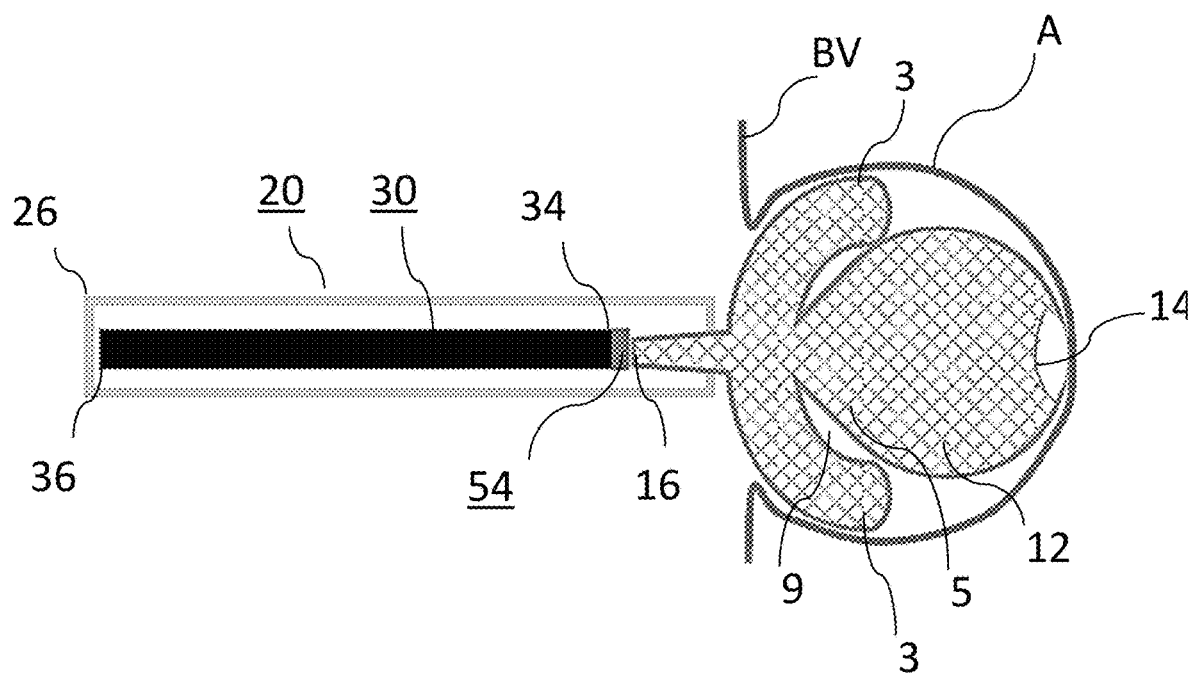
FIG. 5B is an enlarged schematic side view of the delivery system and braid of FIGS. 1-3 as the braid is being pushed into an example aneurysm.

In FIG. 5A, delivery tube 30 has distally translated braid 10 into the aneurysm A. Portion 12 has begun to radially expand towards the outer walls of aneurysm A while unexpanded portion 13 as exited the microcatheter 20 and been inserted inside the aneurysm A at or about the neck. Additionally, parts of braid 10 at or adjacent end 16 are collapsed inside microcatheter 20. The annular expanded segment 3 in FIG. 5A can be seen beginning to expand outwardly from its central axis towards the walls of the aneurysm A while the distal sack of portion 12 expands distal of segment 3. Segment 5 is illustrated as being substantially tubular in FIG. 5A in its pre-expanded state. However, in FIG. 5B as delivery tube 30 moves distally deeper into the aneurysm A, the distal sack of portion 12 and the annular expanded segment 3 continue expanding and inverting about Segment 5 and distal sack 12. Moving between FIGS. 5A to 5B, segment 3 is shown forming about and/or surrounding a lower end of the distal sack of portion 12. Segment 3 is also illustrated overlaying the distal sack of portion 12 in as the braid 10 is distally translated deeper into the aneurysm and end 14 of braid 10 is pushed against the aneurysm wall. As braid 10 is distally translated deeper, it can be seen in FIG. 5B that outer ends of segment 12 begin to press against the annular segment 3.

Figure 6A:
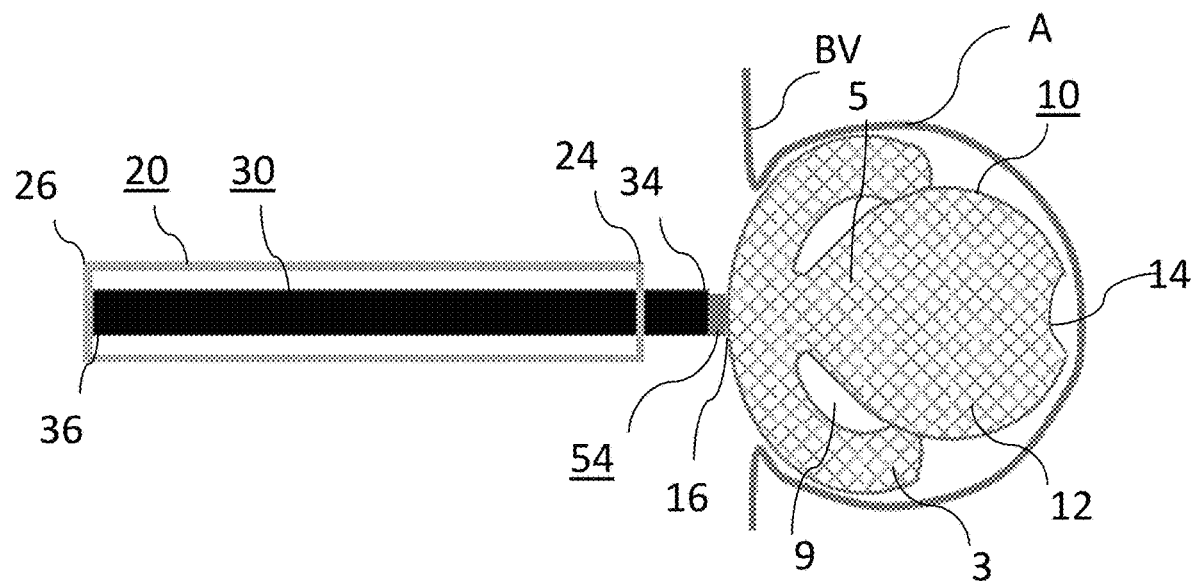
FIG. 6A is an enlarged schematic side view of the delivery system and braid of FIGS. 1-3 as the braid is being pushed into an example aneurysm.

Turning to FIG. 6A, a gap or a cavity 9 has formed between segment 3 and the distal sack as a result of segment 3 inverting about segment 5. This gap or cavity 9 can serve as an "air cushion" that further prevents rupture. Locking portion 54 is depicted proximate or adjacent end 24 of microcatheter 20 so that all portions of braid 10 are distal thereof and external of microcatheter 20. As a result, segment 3 has fully expanded with its distally ends pressed into the distal sack. The proximal surface of segment 3 can be curved or contoured to communicate with the neck of the aneurysm A and function as a flow diverter. It is understood that braid 10 can be made from nitinol with interwoven platinum filaments for radiopacity. Delivery tube 30 may be driven by a hypotube from its proximal end 36 by an operator or the like. During delivery, microcatheter 20 may remain relatively stationary or fixed while delivery tube 30 can be seen distally translating braid 10 towards and through the neck of aneurysm A. As seen in FIG. 6A, further distal translation of delivery tube 30 can essentially cause locking portion 54 to make greater the tapered angle of segment 5 and expansion of segment 3 about portion 12 and/or amount segment 3 is pressed there against. In turn, portion 54 is essentially tucked into braid 10 thereby flattening or otherwise rendering more contoured segment 3 with respect to the neck of the aneurysm.

As also seen moving between FIGS. 5A to 6A, the junction between end 16 of braid 10, locking portion 54, and delivery tube 30 can move from within microcatheter 20 in the collapsed state to completely within aneurysm A in the deployed state. Once braid 10 is selectively positioned, including portions 12 and 13 in their deployed states, braid 10 can be detached from the delivery tube 30 as shown in FIG. 6B. In other words, as the braid 10 is distally translated towards the dome of the aneurysm A, portions 12, 13 can expand to support the aneurysm wall in a manner that is easy, efficient, and avoids risks of rupture.

Figure 6B:
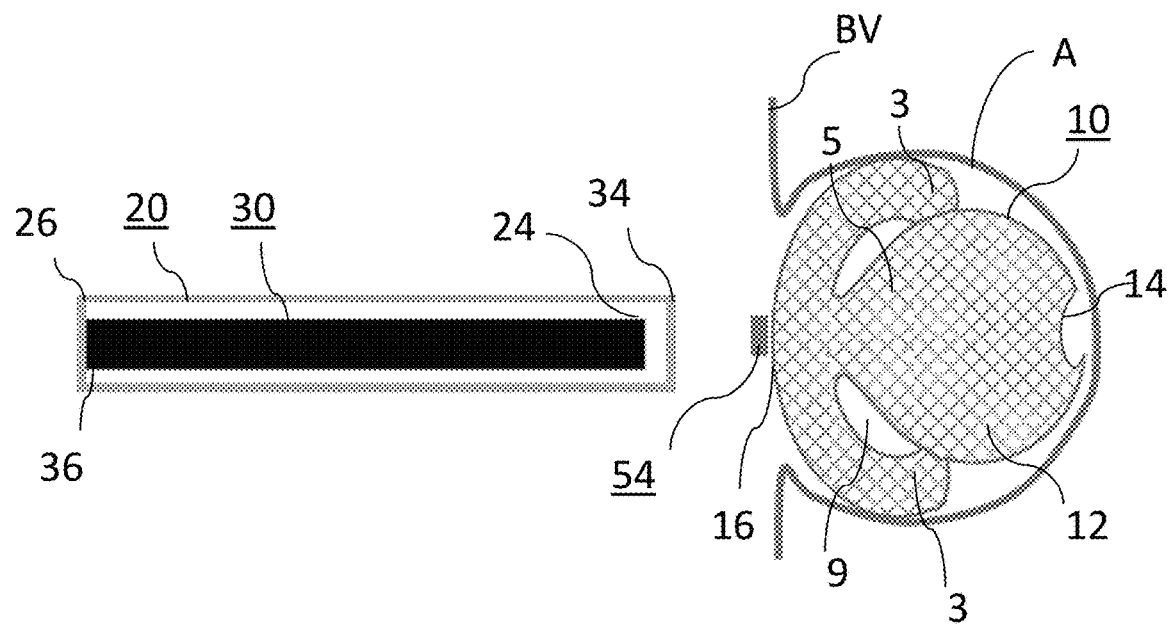
FIG. 6B is an enlarged schematic side view of the delivery system and braid of FIGS. 1-3 as the braid is being pushed into an example aneurysm.

Once expanded and positioned, delivery tube 30 can be proximally translated back into microcatheter 20 and retracted from the braid 10 and aneurysm A. FIG. 6B shows an example arrangement of braid 10 in its deployed state and portions 12 and 13, respectively, moved to their deployed configurations and locking portion 54 detached from delivery tube 30. Expanding portions 12, 13 and/or locking portion 54 into the braid 10 is particularly advantageous as it can prevent braid 10 from creating a protrusion that would otherwise extend into the parent vessel. Instead, any such protrusion can now be tucked into braid 10. Arranging braid 10 in this manner across the neck of the aneurysm while also varying the porosity of portions 12, 13 can also create a flow diversion essentially inside of the sacks of braid 10. FIG. 6B merely shows an example spherical distal sack of portion 12 and an example annular expanded segment 3 fully formed in a manner sufficient to occlude aneurysm A. However, if either portion 12 or 13 is not precisely positioned or needs to be reset or adjusted within aneurysm A for safe occlusion without risk of rupture, braid 10 can be retracted back into microcatheter 20 by proximally withdrawing delivery tube 30 while still attached to braid 10.

Figure 7A:
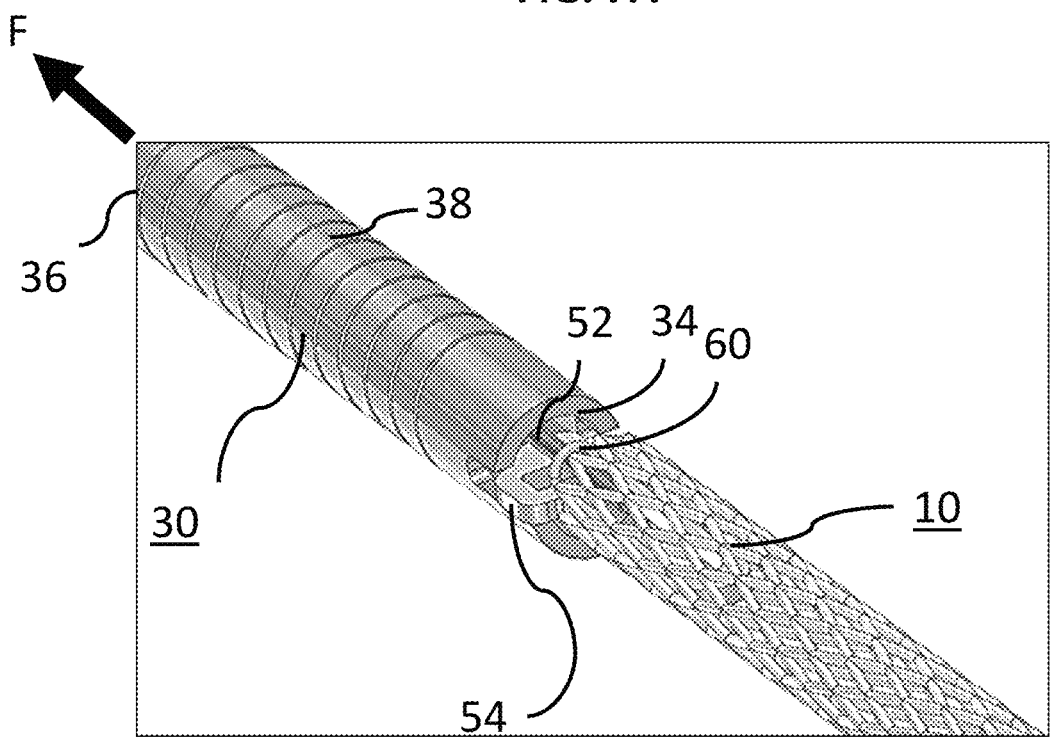
FIG. 7A is a perspective schematic view showing an exemplary delivery system for use with an example occlusive device.

FIGS. 7A to 8B generally illustrate example attachment and delivery between delivery tube 30 and braid 10 for deploying and detaching braid 10 in aneurysm A. The embodiments of FIGS. 7A to 8B is merely one way that delivery tube 30 and braid 10 may be attached at end 34 and any number of attachment means are contemplated as needed or required. The delivery tube 30 as shown can have a lumen extending from a proximal end 36 to a distal, delivery end 34. FIG. 7A illustrates braid 10 engaged with the locking member 52 and loop wire 58 locked into the locking portion 54. The opening 60 of the loop wire 58 can be placed through the locking portion 54. The locking portion 54 preferably takes the form of a small diameter elongate filament, however, other forms such as wires or tubular structures are also suitable. While the locking portion 54 is preferably formed of nitinol, other metals and materials such as stainless steel, PTFE, nylon, ceramic or glass fiber and composites may also be suitable. Locking member 52, in one example, may be an elongated retractable fiber that may extend between ends 24 and 26 of the microcatheter 20. Locking member 52 preferably takes the form of a small diameter elongate filament, however, other forms such as wires or tubular structures are also suitable. While the locking member 52 is preferably formed of nitinol, other metals and materials such as stainless steel, PTFE, nylon, ceramic or glass fiber and composites may also be suitable. When the locking member 52 is put through the opening 60 the braid 10 is now secure. It is understood that delivery tube 30 may include a compressible portion 38 disposed between its ends 34 and 36.

The compressible portion 38 can allow the delivery tube 30 to bend and/or flex. Such flexibility can assist tracking the braid 10 through the microcatheter 20 and the tortuous path through the vasculature. The compressible portion 38 can be formed with interference spiral cuts that can allow for gaps to permit bending but in one example, do not act as a spiral-cut spring. Compressible portion 38 can be axially adjustable between an elongated condition and a compressed condition. However, any other arrangement allowing axial adjustment (e.g., a wound wire or spiral ribbon) can also be suitable for use with detachment systems according to the present disclosure). The compressible portion 38 can be in the elongated condition at rest and automatically or resiliently returns to the elongated condition from a compressed condition, unless otherwise constrained. The function of the compressible portion 38 is described in greater detail herein.

Figure 7B:
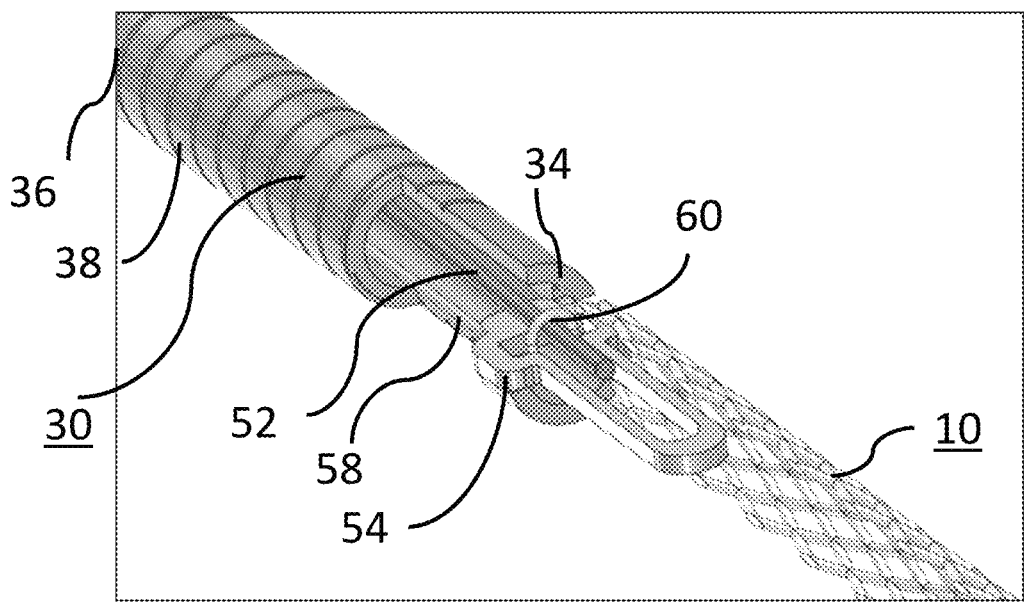
FIG. 7B is a perspective schematic view of FIG. 7A but with partial cross-section of the delivery system and the occlusive device.
Figure 8A:
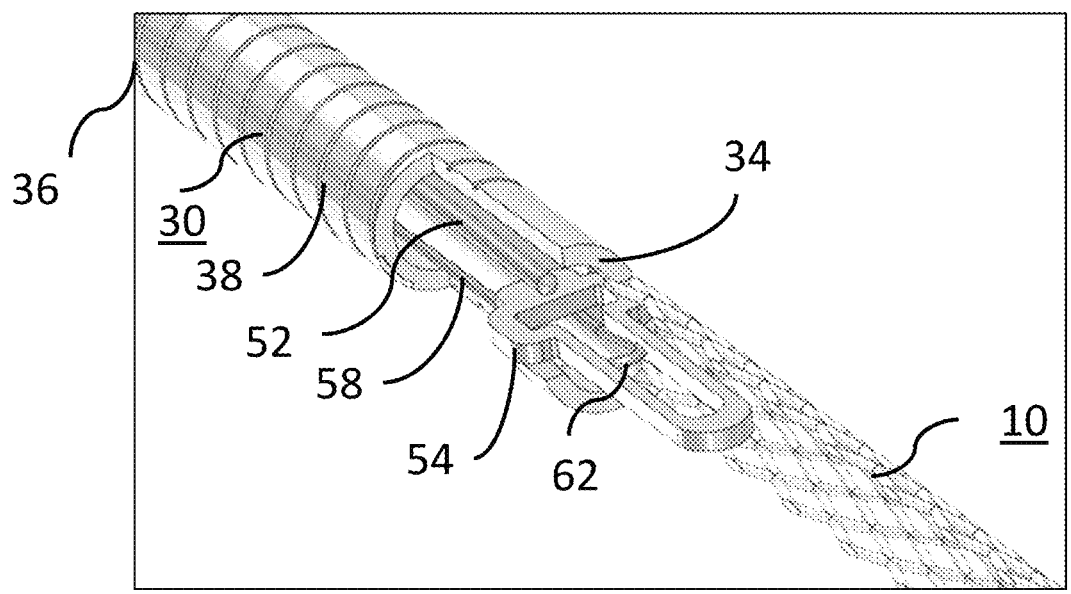
FIG. 8A is a perspective schematic view of FIGS. 7A-7B being deployed with partial cross-section of the delivery system and the occlusive device.
Figure 8B:
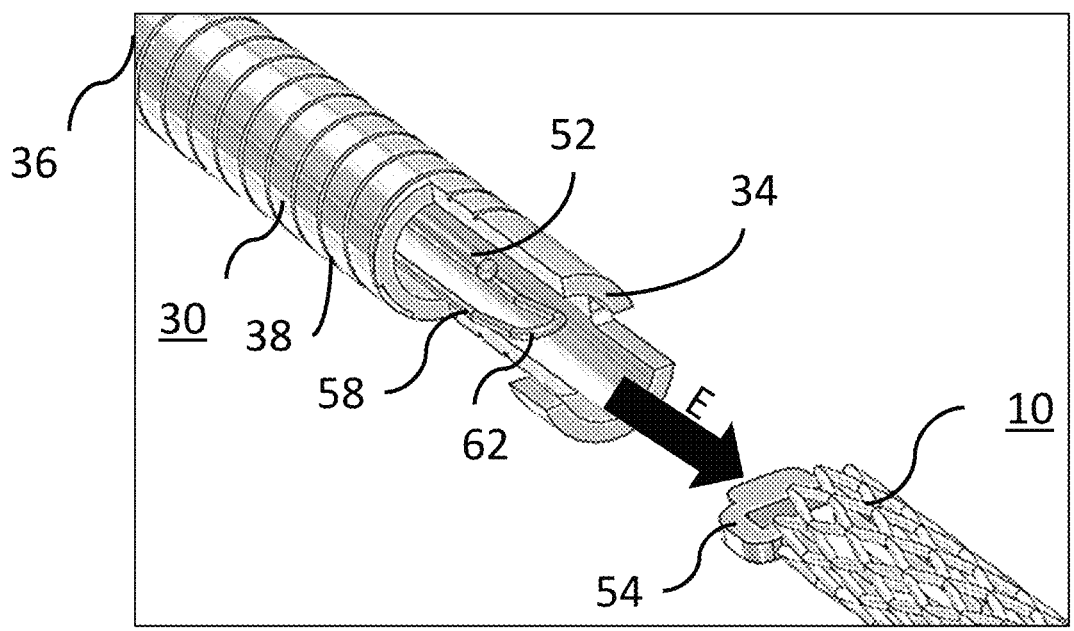
FIG. 8B is a perspective schematic view of FIGS. 7A-7B deployed with the exemplary delivery system detached from the occlusive device.

In FIG. 7A, a force F was previously applied to place the delivery tube 30 in a compressed state. FIG. 7B illustrates the locking member 52 being drawn proximally to begin the release sequence for braid 10. FIG. 8A illustrates the instant the locking member 52 exits the opening 60 and is pulled free of the loop wire 58. The distal end 62 of the loop wire 58 falls away/returns to its preformed shape and exits the locking portion 54. As can be seen, there is now nothing holding the braid 10 to the delivery tube 30. FIG. 8B illustrates the end of the release sequence. Here, the compressible portion 38 of the delivery tube 30 has expanded/returned to its original shape and "sprung" forward. An elastic force E is imparted by the distal end 34 of the delivery tube 30 to the braid 10 to "push" it away to insure a clean separation and delivery of the braid 10 to the aneurysm A. It is to be understood that the delivery scheme described in FIGS. 7A-8B are merely example approaches to delivery of braid 10.

Figure 9:
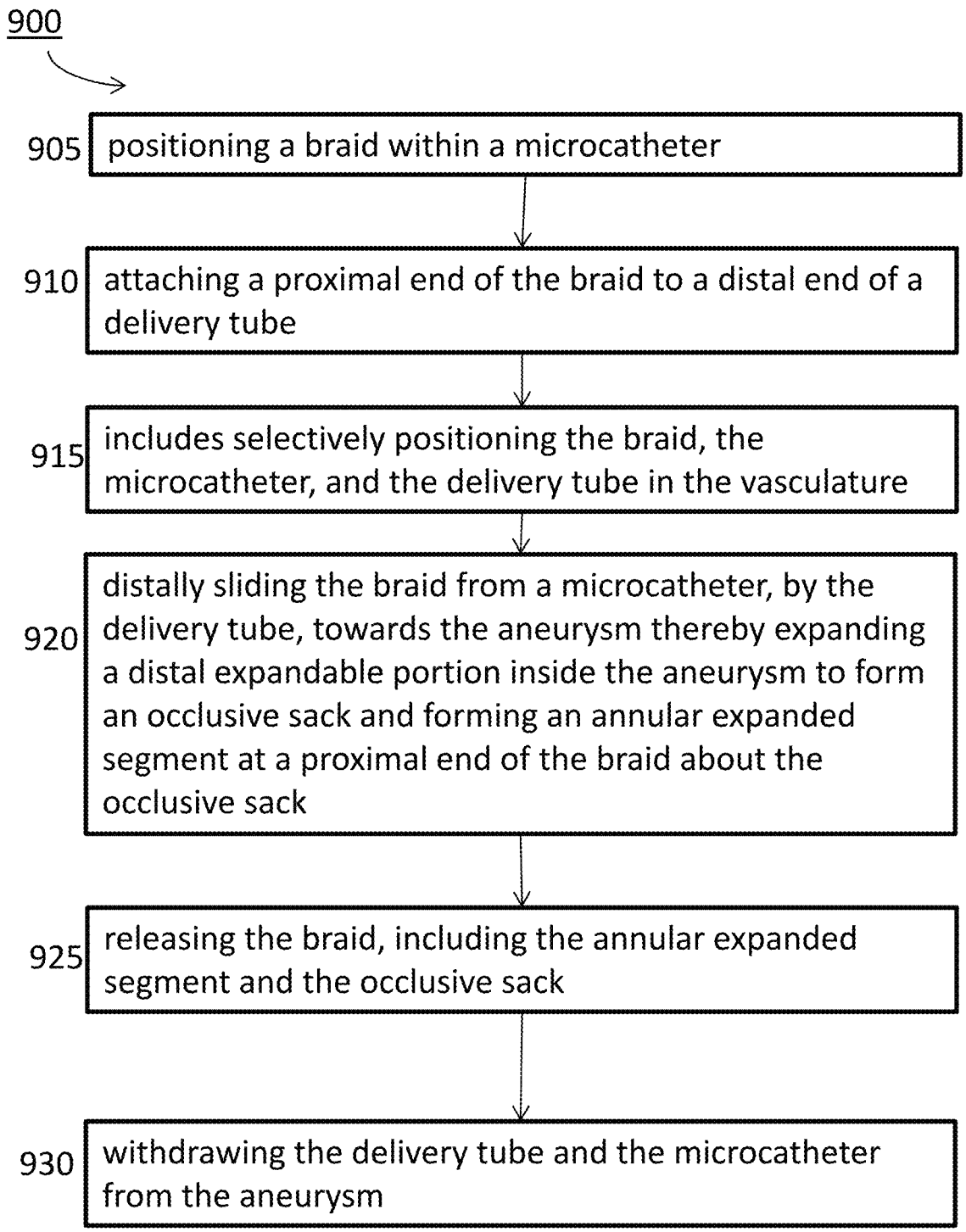
FIG. 9 is a flow diagram for a method of delivering an occlusive device.
Figure 10:
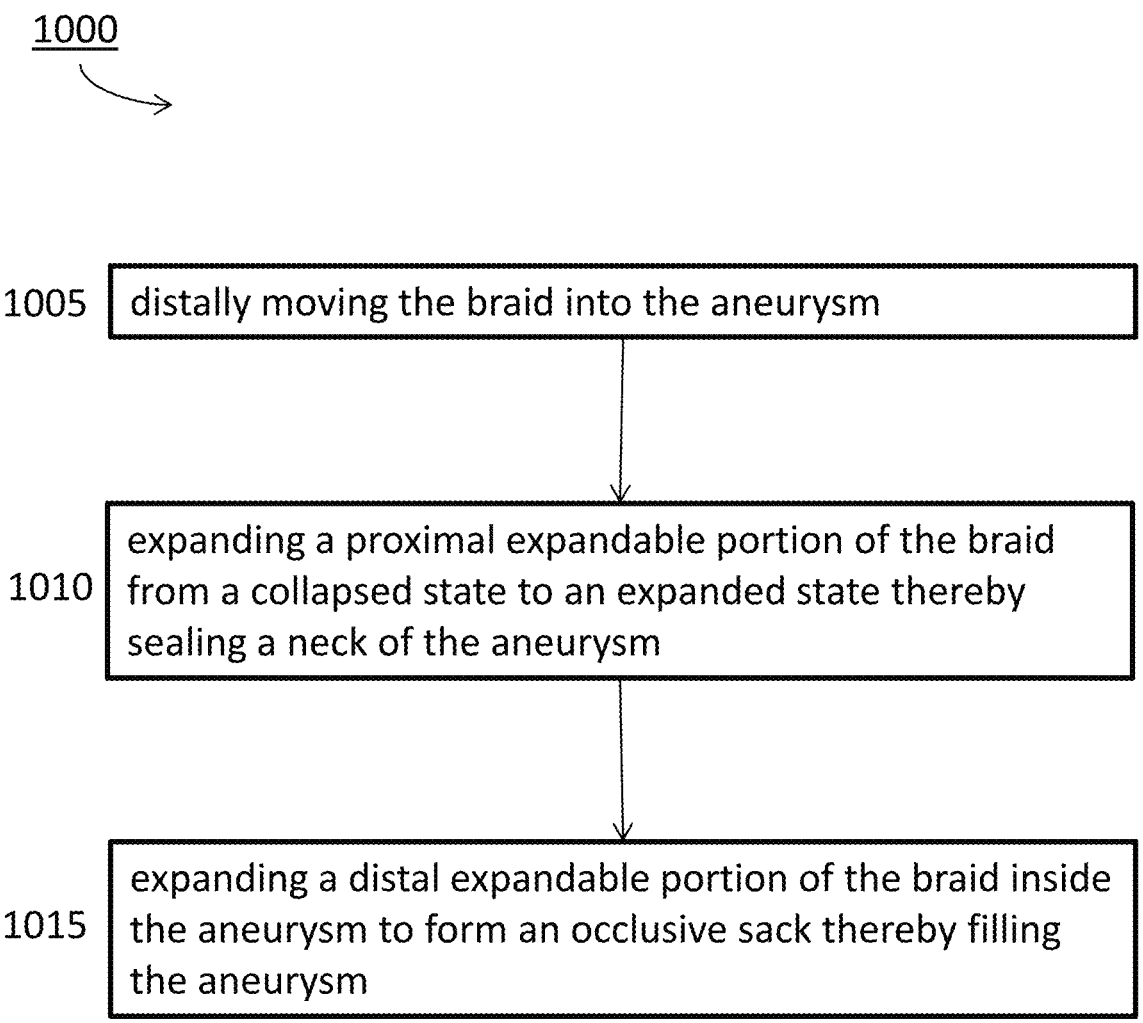
FIG. 10 is a flow diagram for a method of delivering an occlusive device.

FIG. 9 is a flow diagram for a method 900 of delivering an occlusive device to the aneurysm. Step 905 includes attaching a proximal end of the braid to a distal end of a delivery tube. Step 910 includes selectively positioning the microcatheter in the vasculature (e.g. at the neck of the aneurysm). Step 915 includes positioning the braid with attached delivery tube in microcatheter. Step 920 includes distally sliding the braid from a microcatheter, by the delivery tube, towards the aneurysm thereby expanding a distal expandable portion inside the aneurysm to form a distal sack and forming an annular expanded segment at a proximal end of the braid about the distal sack. Step 925 includes releasing the braid, which can include the annular expanded segment and the distal sack. Step 930 includes withdrawing the delivery tube and the microcatheter from the aneurysm.

In certain embodiments, the method 900 can also include filling the aneurysm by forming the distal sack. In some embodiments, the selectively positioning of the braid comprises placing a distal end of the microcatheter at the neck of the aneurysm. In some embodiments, the distal expandable portion is simultaneously expanding when the annular expanded segment is forming.

In certain embodiments, the method 900 can also include attaching the locking portion at the proximal end of the braid and the distal end of the delivery tube; and releasing, by the locking portion, the delivery tube from the braid. In certain embodiments, the method 900 can also include expanding the annular expanded segment so that the annular expanded segment overlays an outer surface of the distal sack. In certain embodiments, the method 900 includes pressing one or more outer ends of the distal sack against the annular expanded segment as the braid distally translates into the aneurysm. In certain embodiments, the method 900 includes forming a gap or a cavity between the annular expanded segment and the distal sack when the annular expanded segment is inverted about the distal sack. In certain embodiments, the method 900 includes forming a tapered segment between the proximal and distal expandable portions.

In certain embodiments, the method 900 also includes making a porosity of the proximal expandable portion less than a porosity of the tapered segment and/or the distal expandable portion; positioning the proximal expandable portion adjacent or in communication with a neck of the aneurysm; and deflecting, diverting, and/or slowing a flow into the aneurysm. The method 900 can also include making a flexibility of the proximal expandable portion less than a flexibility of the tapered segment and/or the distal expandable portion; positioning the proximal expandable portion adjacent or in communication with a neck of the aneurysm; and deflecting, diverting, and/or slowing a flow into the aneurysm.

In some embodiments, a method 1000 of using a braid for treating an aneurysm is disclosed. Step 1005 can include distally moving the braid into the aneurysm. Step 1010 can include expanding a proximal expandable portion of the braid from a collapsed state to an expanded state thereby sealing a neck of the aneurysm. Step 1015 can include expanding a distal expandable portion of the braid inside the aneurysm to form a distal sack thereby filling the aneurysm.

In certain embodiments, step 1015 can include forming an annular expanded segment at a proximal end of the braid about the distal sack. In some embodiments, the method 1000 can include overlaying and inverting the annular expanded segment about an outer surface of the distal sack. In some embodiments, the method 1000 can include forming a gap or a cavity between the annular expanded segment and the distal sack when the annular expanded segment inverts about the distal sack. In some embodiments, the method 1000 can include forming a tapered segment between the proximal and distal expandable portions. The method 1000 can also include making a porosity of the proximal expandable portion less than a porosity of the tapered segment and/or the distal expandable portion; and deflecting, diverting, and/or slowing a flow into the aneurysm. The method 1000 can also include making a flexibility of the proximal expandable portion less than a flexibility of the tapered segment and/or the distal expandable portion; and deflecting, diverting, and/or slowing a flow into the aneurysm.

It is understood that variations of the braid 10 can include various materials such as stainless steel, bio absorbable materials, and polymers. Braid 10, including any specific portions such as any breaks, varying regions of differing porosities, and occlusive sacks, can be heat set to various configurations such as spherical, oblong, saddle shaped, or the like, for shaping the distal sack and/or other expanded segment(s) to better match the aneurysm morphology. In addition, the braid 10 can be heat shaped to include weak points to facility the radial expansion of the distal sack and/or other expanded segment(s). Further, interstices of braid 10 that form the distal sack and/or other expanded segment(s) can vary, or be selectively designed, in size or shape along its length depending on how much braid 10 is caused to expand as delivery tube 30 is distally moved.

It is understood that the braid 10 can also be included in a system or otherwise in communication with an imaging device capable of imaging the distal sack and/or other expanded segment(s) of braid 10 with respect to the aneurysm. An orientation of the distal sack and/or other expanded segment(s) can be adjustable by the braid 10 being distally or proximally moved with respect to the aneurysm and monitored precisely by the imaging device through one or more radiopaque features of the braid or attached thereto.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A braid for occluding an aneurysm, the braid comprising:
a proximal expandable portion comprising:
a collapsed state where the proximal portion is substantially tubular housed within a lumen of a microcatheter;
a deployed state for positioning inside the aneurysm and sealing across a neck of the aneurysm, the proximal expandable portion in the deployed state configured to expand radially from being substantially tubular; and
a distal expandable portion distal of the proximal expandable portion, the distal expandable portion being substantially tubular and continuous with the proximal expandable portion in the collapsed state, the distal expandable portion comprising an open distal end disposed distally from a distal end of the proximal expandable portion in the deployed state;
the distal expandable portion configured in the deployed state to fill the aneurysm and provides an outward force on the proximal portion for it to remain in place in the aneurysm;
wherein distally translating the braid in the aneurysm as a distal sack is formed by the distal expandable portion causes an annular expanded segment of the proximal expandable portion to radially expand, invert, and surround a proximal end of the distal sack.

2. The braid of claim 1, wherein the annular expanded segment forms, inverts about and surrounds a lower end of the distal sack.

3. The braid of claim 1, wherein a porosity of the proximal expandable portion is less than a porosity of the distal expandable portion.

4. The braid of claim 3, wherein the respective porosities are defined by at least one of dimensions of interstices, braid angle, heat treatment, and covering.

5. The braid of claim 1, wherein the annular expanded segment overlays external to the distal sack whereby outer ends of the distal sack are capable of pressing against the inner surface of the annular expanded segment as the braid expands into the deployed state.

6. The braid of claim 5, wherein a gap or a cavity is formed between the annular expanded segment and the distal sack when the annular expanded segment is inverted about the distal sack.

7. The braid of claim 1, further comprising a tapered segment disposed between the proximal and distal expandable portions.

8. The braid of claim 7, wherein the proximal expandable portion comprises a porosity lower than a porosity of the tapered segment and the distal expandable portion.

9. The braid of claim 7, further comprising a buckle portion defined between the tapered segment and the proximal expandable portion or the distal expandable portion.

10. A system for treating an aneurysm, the system comprising:
a microcatheter;
a delivery tube translatably disposed in the microcatheter; and
a braid according to claim 1, the braid being detachably connected to the delivery tube and slideably disposed within the microcatheter in a collapsed state and distally translatable from within the microcatheter to a deployed state;
wherein the braid expands, including at least one of a distal and a proximal expandable portion, to the deployed state as the distal end of the braid distally exits the microcatheter.

11. The system of claim 10, wherein the annular expanded segment overlays external to the distal sack as the braid distally translates from the microcatheter and the braid is pushed against the aneurysm wall.

12. A method, comprising:
distally sliding the braid according to claim 1, by a delivery tube, from the microcatheter towards the aneurysm thereby
expanding the distal expandable portion inside the aneurysm to form the distal sack; and
forming the annular expanded segment at a proximal end of the braid about the occlusive sack by inversion.

13. The method of claim 12, further comprising:
filling the aneurysm by forming the distal sack.

14. The method of claim 12, further comprising:
attaching a locking portion to the delivery tube at the proximal end of the braid and the distal end of the delivery tube; and
releasing, by the locking portion, the delivery tube from the braid.

15. The method of claim 12, further comprising:
expanding the annular expanded segment so that the annular expanded segment overlays an outer surface of the distal sack.

16. The method of claim 15, further comprising:
pressing one or more outer ends of the outer surface of the distal sack against the annular expanded segment as the braid distally translates into the aneurysm.

17. The method of claim 16, further comprising:
forming at least one of a gap or a cavity between the annular expanded segment and the distal sack when the annular expanded segment inverts about the outer surface of the occlusive sack.

18. The method of claim 12, further comprising:
making a porosity of the proximal expandable portion less than a porosity of at least one of a tapered segment between the proximal and distal expandable portions;
positioning the proximal expandable portion adjacent or in communication with the neck of the aneurysm; and
deflecting, diverting, or slowing a flow into the aneurysm.

19. A method of occluding an aneurysm, comprising:
distally moving a braid according to claim 1, into the aneurysm;
expanding the proximal expandable portion of the braid from the collapsed state to the deployed state thereby sealing a neck of the aneurysm; and
expanding the distal expandable portion of the braid inside the aneurysm to form the distal sack thereby filling the aneurysm.

* * * * *